US009764191B2

(12) United States Patent
Oshima et al.

(10) Patent No.: US 9,764,191 B2
(45) Date of Patent: Sep. 19, 2017

(54) TRAINING APPARATUS

(71) Applicant: MURATA MACHINERY, LTD., Kyoto-shi, Kyoto (JP)

(72) Inventors: Osamu Oshima, Kyoto (JP); Hiroaki Ohmatsu, Kyoto (JP)

(73) Assignee: MURATA MACHINERY, LTD., Kyoto (JP)

( * ) Notice: Subject to any disclaimer, the term of this patent is extended or adjusted under 35 U.S.C. 154(b) by 41 days.

(21) Appl. No.: 14/881,035

(22) Filed: Oct. 12, 2015

(65) Prior Publication Data
US 2016/0121166 A1 May 5, 2016

(30) Foreign Application Priority Data

Oct. 29, 2014 (JP) ................. 2014-220070

(51) Int. Cl.
*A63B 24/00* (2006.01)
*A63B 23/12* (2006.01)
(Continued)

(52) U.S. Cl.
CPC .......... *A63B 24/0087* (2013.01); *A61B 5/221* (2013.01); *A61B 5/224* (2013.01); *A61H 1/0237* (2013.01); *A61H 1/0274* (2013.01); *A63B 21/0058* (2013.01); *A63B 21/00072* (2013.01); *A63B 21/00178* (2013.01); *A63B 21/4017* (2015.10); *A63B 21/4033* (2015.10); *A63B 21/4035* (2015.10); *A63B 21/4047* (2015.10); *A63B 23/03508* (2013.01); *A63B 23/1281* (2013.01); *A63B 24/0006* (2013.01); *A63B 24/0062* (2013.01); *G06F 19/3481* (2013.01);
(Continued)

(58) Field of Classification Search
CPC ............ A63B 24/0087; A63B 24/0062; A63B 23/0355; A63B 24/0006; A63B 2024/0065; A61B 5/221; A61B 5/224; A61B 2505/09; A61B 5/11
See application file for complete search history.

(56) References Cited

U.S. PATENT DOCUMENTS 5,466,213 A * 11/1995 Hogan ..................... A61H 1/02
482/4
5,755,645 A * 5/1998 Miller ................. A61H 1/0285
482/115
(Continued)

FOREIGN PATENT DOCUMENTS

WO 2012/117488 A1 9/2012

*Primary Examiner* — Sundhara Ganesan
(74) *Attorney, Agent, or Firm* — DLA Piper LLP (US)

(57) ABSTRACT

A training apparatus includes an operating rod, a strength detector, a motion position detector, a strength speed calculator, a boundary line arrival speed calculator, and a motion speed calculator. The operating rod moves a held limb. The strength detector outputs a strength component signal based on a magnitude of a strength component. The motion position detector detects a motion position of the operating rod. The strength speed calculator calculates a strength speed. The boundary line arrival speed calculator calculates a boundary line arrival speed whose absolute value is smaller as a boundary line distance is shorter. The motion speed calculator calculates a lower one of the strength speed and the boundary line arrival speed as the motion speed at which the operating rod should move.

4 Claims, 27 Drawing Sheets

(51) Int. Cl.
*A61H 1/02* (2006.01)
*A63B 21/00* (2006.01)
*G06F 19/00* (2011.01)
*A61B 5/22* (2006.01)
*A63B 21/005* (2006.01)
*A63B 23/035* (2006.01)
*A61B 5/11* (2006.01)
*A63B 71/06* (2006.01)

(52) U.S. Cl.
CPC ............ *A61B 5/11* (2013.01); *A61B 2505/09* (2013.01); *A61H 2201/1207* (2013.01); *A61H 2201/1659* (2013.01); *A61H 2201/5035* (2013.01); *A61H 2201/5038* (2013.01); *A61H 2201/5043* (2013.01); *A61H 2201/5046* (2013.01); *A61H 2201/5048* (2013.01); *A61H 2201/5061* (2013.01); *A61H 2201/5064* (2013.01); *A61H 2201/5069* (2013.01); *A63B 23/0355* (2013.01); *A63B 71/0622* (2013.01); *A63B 2024/0071* (2013.01); *A63B 2024/0093* (2013.01); *A63B 2208/0247* (2013.01); *A63B 2220/13* (2013.01); *A63B 2220/20* (2013.01); *A63B 2220/30* (2013.01); *A63B 2220/31* (2013.01); *A63B 2220/34* (2013.01); *A63B 2220/40* (2013.01); *A63B 2220/51* (2013.01); *A63B 2230/436* (2013.01)

(56) References Cited

U.S. PATENT DOCUMENTS

| | | | | |
|---|---|---|---|---|
| 5,830,160 | A | * | 11/1998 | Reinkensmeyer ..... A61B 5/224 600/595 |
| 6,270,445 | B1 | * | 8/2001 | Dean, Jr. ............ A61H 1/0259 482/114 |
| 6,613,000 | B1 | * | 9/2003 | Reinkensmeyer ..... A61B 5/221 600/587 |
| 8,012,107 | B2 | | 9/2011 | Einav et al. |
| 8,753,296 | B2 | | 6/2014 | Einav et al. |
| 2008/0282228 | A1 | * | 11/2008 | Subramanyam .......... G06F 8/20 717/121 |
| 2014/0135174 | A1 | * | 5/2014 | Potash ............... A63B 24/0087 482/8 |

* cited by examiner

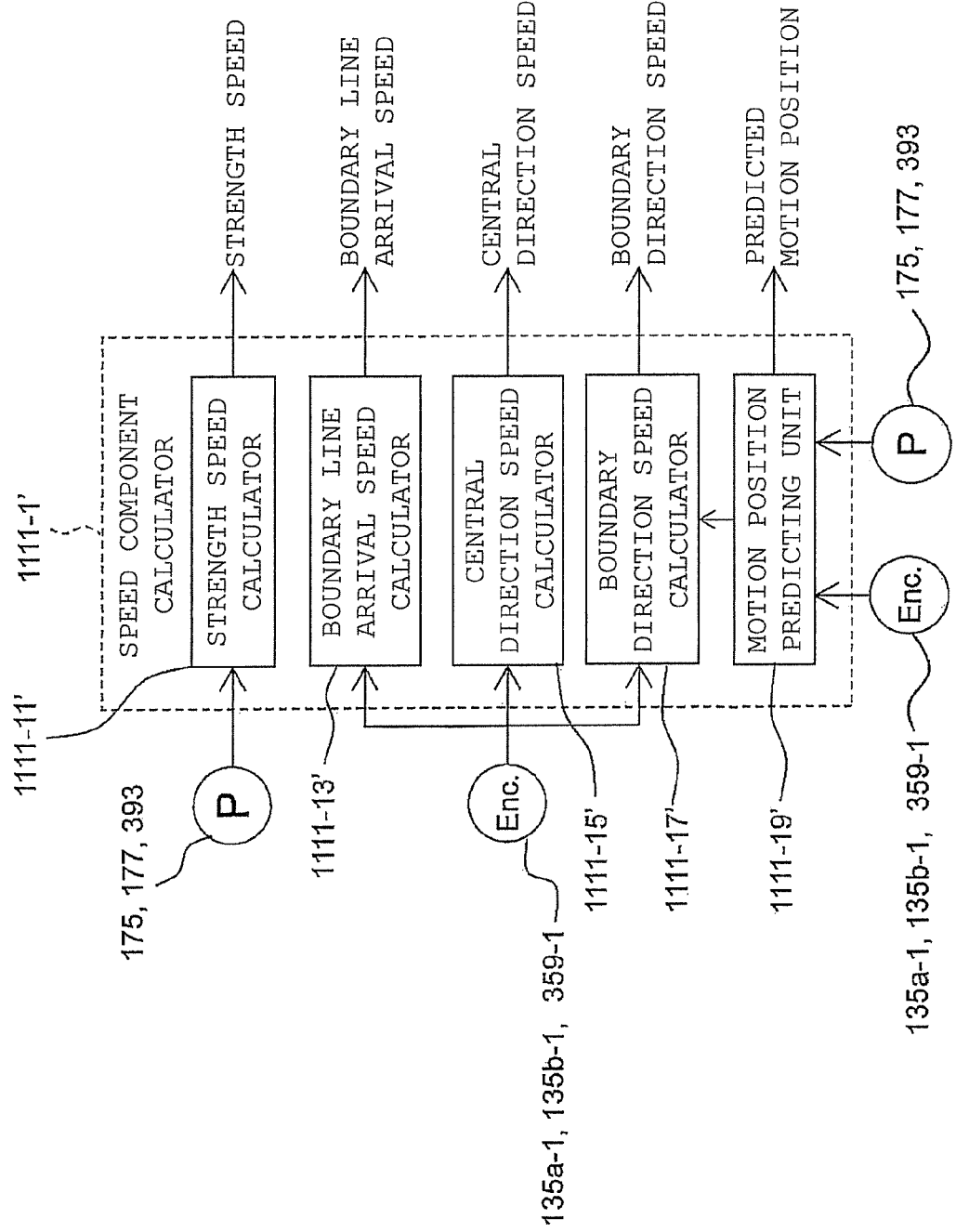

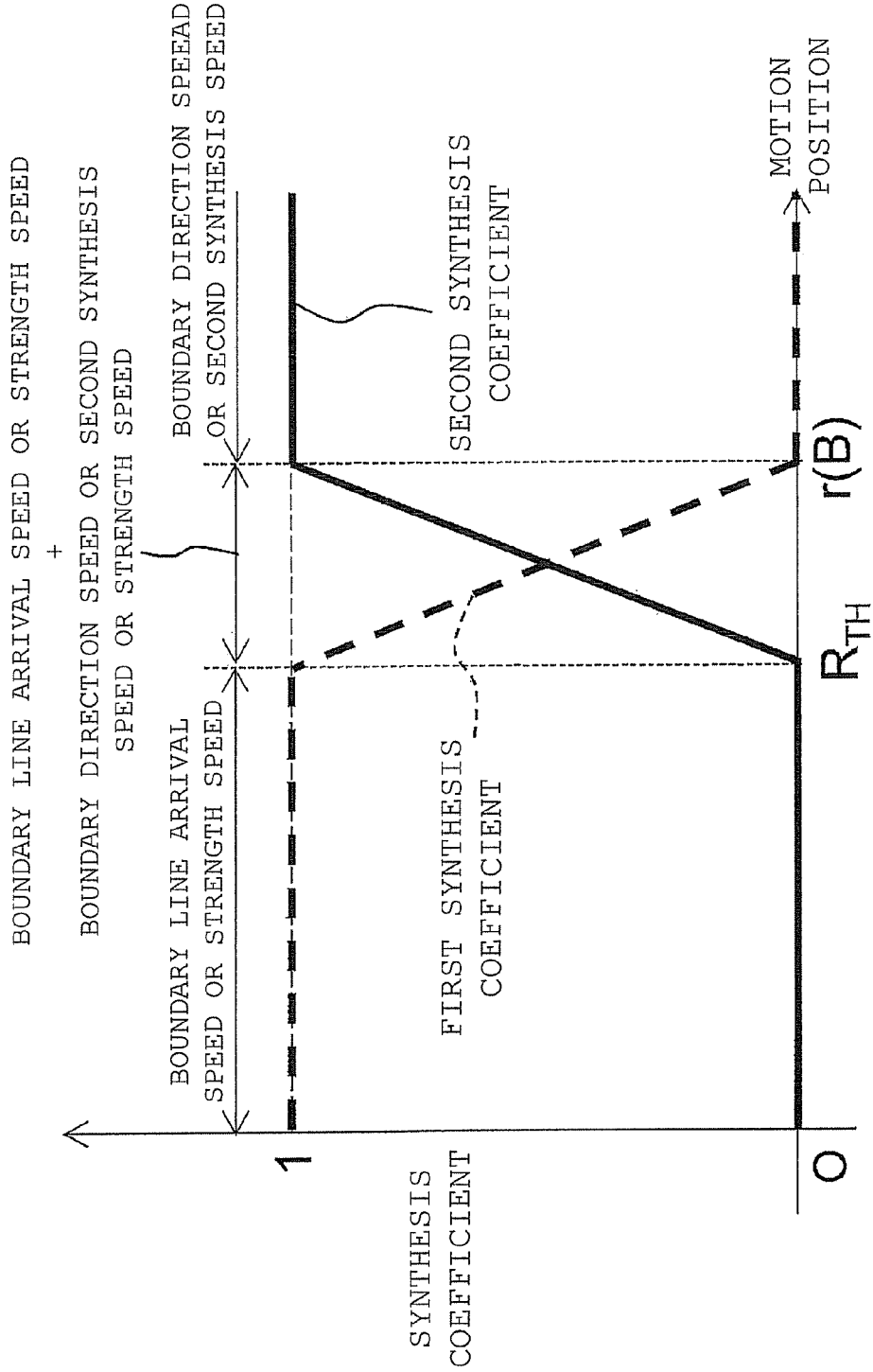

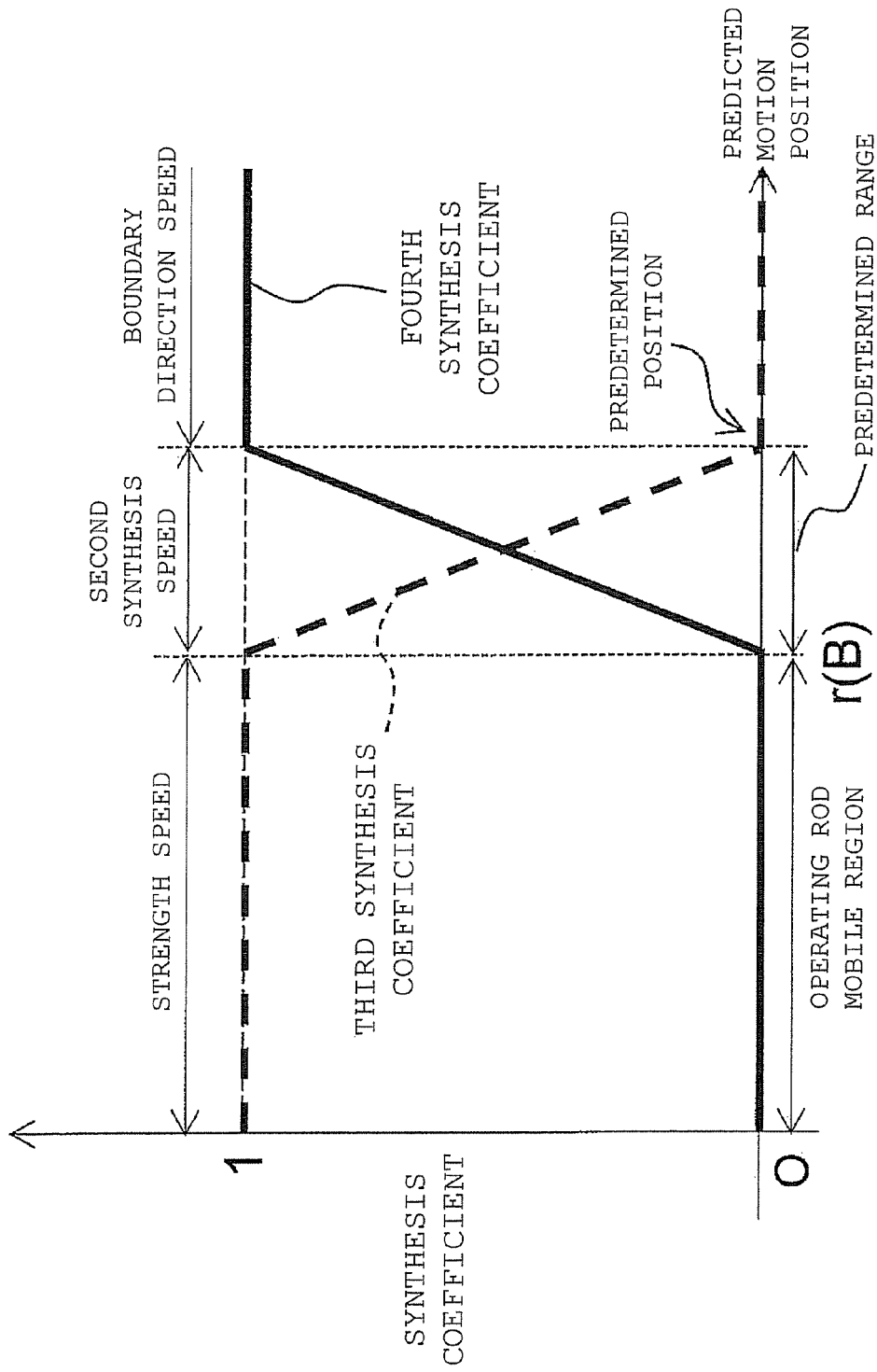

TRAINING APPARATUS

CROSS-REFERENCE TO RELATED APPLICATIONS

This application claims priority under 35 U.S.C. 119 to Japanese Patent Application No. 2014-220070, filed on Oct. 29, 2014, which application is hereby incorporated by reference in its entirety.

BACKGROUND OF THE INVENTION

1. Field of the Invention

The present invention relates to a training apparatus for supporting rehabilitation on patient's upper limb and lower limb according to a predetermined training program.

2. Description of Related Art

Since the rehabilitation aimed at motor function recovery of a stroke patient's hemiplegic upper limb or lower limb is generally provided by an occupational therapist or a physical therapist, efficient provision of the rehabilitation is limited. For example, in the rehabilitation aimed at the motor function recovery of an upper limb, an accurate movement of a paralyzed upper limb is mainly required to be passively and actively repeated to the utmost extent in a slightly wider range than a current range. An occupational therapist or physical therapist teaches a patient an accurate movement, and guides the patient an active movement while applying a passive load to a patient's upper limb through a procedure based on the rehabilitation relating to the motor function recovery.

In such rehabilitation, a repetition of the movement is limited due to therapist's physical limit. Further, a difference might be caused in a medical care quality of the rehabilitation according to therapist's experience. Therefore, for example, an upper limb training apparatus for supporting rehabilitation on a patient whose limb, such as an arm, is physically disabled is described in WO 2012/117488 A in order to support training provided by a therapist, eliminate restriction due to fatigue and normalize medical care quality as possible. This apparatus includes a stationary frame that can be arranged on a floor surface, a movable frame supported to the stationary frame so as to be capable of tilting in an omnidirectional way, and an operating rod that is telescopically attached to the movable frame and is manipulated by a person who undergoes training.

In the training apparatus disclosed in WO 2012/117488 A, a motion range of the operating rod (an operating rod mobile region) is set so that a patient does not fall from a chair during the training. In a conventional training apparatus, a motion speed of the operating rod is 0 at a time point when the operating rod arrives at a boundary of the operating rod mobile region.

For this reason, in a conventional training apparatus, when the patient moves the operating rod to the boundary of the operating rod mobile region, the operating rod exerts an impact on the patient's limb. Such an impact exerted on patient's limb from the operating rod is not preferable from a viewpoint of motor function recovery of the limb.

BRIEF SUMMARY OF THE INVENTION

According to the present invention, in a training apparatus for training a limb, when an operating rod arrives at a boundary of an operating rod mobile region, an impact is restrained from being exerted on the limb and the operating rod is restrained from moving outside the mobile region.

A plurality of modes are described below. These modes can form any combinations as necessary. A training apparatus according to one aspect of the present invention is a training apparatus for training a patient's four limbs including upper limbs and/or lower limbs according to a predetermined training program. The training apparatus includes an operating rod, a strength detector, a motion position detector, a strength speed calculator, a boundary line arrival speed calculator, and a motion speed calculator.

The operating rod is supported to a stationary frame placed on a floor surface or near the floor surface so as to be movable at 1 or more degrees of freedom. Further, the operating rod moves a held limb. The strength detector detects a strength component and outputs a strength component signal based on a magnitude of the detected strength component. The strength component is a component in each freedom degree direction of a strength applied to the operating rod at which the operating rod is movable. The motion position detector detects a motion position of the operating rod. The motion position of the operating rod is a position of the operating rod in each related freedom degree direction at which the operating rod is movable.

The strength speed calculator calculates a strength speed of the operating rod based on the strength component signal output from the strength detector. The boundary line arrival speed calculator calculates a boundary line arrival speed whose absolute value is smaller as a boundary line distance is shorter. The boundary line distance is a distance from a current motion position of the operating rod to a mobile region boundary line. The mobile region boundary line is a boundary line for setting a boundary of the operating rod mobile region. The operating rod mobile region is a region for setting a movable range of the operating rod.

The motion speed calculator calculates the lower one of the strength speed and the boundary line arrival speed as a motion speed. The motion speed is a speed at which the operating rod should operate.

In the training apparatus, first, the motion position detector detects a current motion position of the operating rod, and the strength detector detects a strength. After the current motion position and the strength are detected, the strength speed calculator calculates a strength speed based on the strength component signal, and the boundary line arrival speed calculator calculates a boundary line arrival speed based on the boundary line distance. Thereafter, the motion speed calculator calculates the lower one of the strength speed and the boundary line arrival speed as a motion speed.

In the training apparatus, the boundary line arrival speed whose absolute value is smaller as the boundary line distance is shorter, and the strength speed based on the strength are calculated, and the lower one of the boundary line arrival speed and the strength speed is selected as the motion speed of the operating rod. That is, the motion speed of the operating rod is limited to the lowest one of the calculated speed components. Further, the motion speed is limited by the boundary line arrival speed whose absolute value is smaller as the boundary line distance is shorter particularly near the mobile region boundary line. As a result, when the operating rod arrives at the mobile region boundary line, the operating rod can be restrained from abruptly stopping to exert an impact on the limb and the operating rod can be restrained from moving outside the operating rod mobile region.

Further, when the lower one of the strength speed and the boundary line arrival speed is selected as the motion speed, the motion speed can be smoothly switched from the strength speed into the boundary line arrival speed (or vice versa). As a result, the motion speed of the operating rod can be switched without exerting an impact on the limb.

The motion speed may be limited to a maximum motion speed or less. The maximum motion speed is a speed for determining an upper limit value of the motion speed of the operating rod. As a result, the operating rod can be restrained from moving at an excessively high speed.

When a determination is made that the current motion position of the operating rod is present outside the operating rod mobile region, the motion speed calculator may calculate a motion speed including a speed component directing toward a motion position reference point. The motion position reference point is a reference point of the motion position of the operating rod. As a result, the operating rod can be restrained from moving further outside the operating rod mobile region, and the operating rod can be restrained from being disabled with the current motion position of the operating rod being present outside the operating rod mobile region. Further, the operating rod outside the operating rod mobile region is returned into the operating rod mobile region.

According to the above modes, in the training apparatus, when the operating rod arrives at the boundary of the operating rod mobile region, an impact can be restrained from being exerted on the limb and the operating rod can be restrained from moving outside the operating rod mobile region.

These and other elements, features, steps, characteristics and advantages of the present invention will become more apparent from the following detailed description of various embodiments of the invention with reference to the attached drawings.

BRIEF DESCRIPTION OF THE DRAWINGS

FIG. 14A is a diagram illustrating a configuration of a speed component calculator of the training apparatus according to a second embodiment;

FIG. 16B is a diagram illustrating a relationship between a first synthesis coefficient and a second synthesis coefficient and a distance from a motion position reference point to the motion position;

FIG. 17B is a diagram illustrating a relationship between a third synthesis coefficient and a fourth synthesis coefficient and a distance from the motion position reference point to a predicted motion position;

DETAILED DESCRIPTION OF PREFERRED EMBODIMENTS

1. First Embodiment (1) Entire Configuration of Training Apparatus

Figure 1:
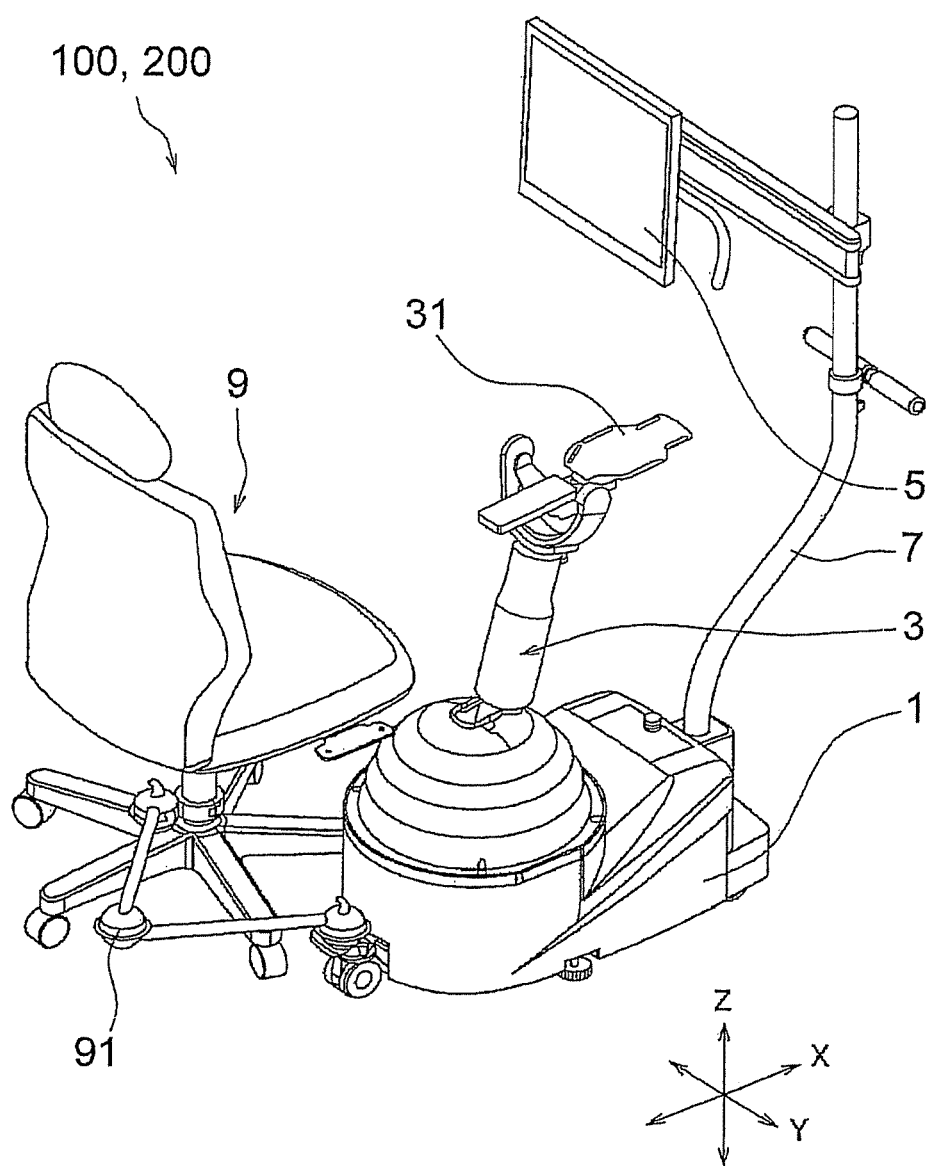
FIG. 1 is a diagram illustrating an entire configuration of a training apparatus.

A training apparatus of the present invention is described below. An entire configuration of a training apparatus 100 according to a first embodiment is described first with reference to FIG. 1. FIG. 1 is a diagram illustrating the entire configuration of the training apparatus 100. The training apparatus 100 is a training apparatus for conducting training for the purpose of a motor function recovery of any limb of a user's (patient's) four limbs including upper limbs and/or lower limbs according to a predetermined training program. The training apparatus 100 mainly includes a stationary frame 1, an operating rod 3, and a training instructing unit 5. The stationary frame 1 is placed on or adjacent to a floor surface where the training apparatus 100 is installed. Further, the stationary frame 1 forms a main body case of the training apparatus 100.

The operating rod 3 is mounted to the stationary frame 1 via an operating rod tilting mechanism 13 (FIG. 2) provided in the stationary frame 1. As a result, the operating rod 3 can be moved (tilted) in an X-axis direction parallel with a lengthwise direction of the stationary frame 1 and a Y-axis direction (FIG. 1 and FIG. 2) parallel with a widthwise direction of the stationary frame 1 by the operating rod tilting mechanism 13. The operating rod 3 may be moved (tilted) only in the X-axis direction or the Y-axis direction as needed. In this case, the operating rod 3 can be tilted at 1-degree-of-freedom.

Further, the operating rod 3 may include an expansion mechanism (FIG. 5) in a lengthwise direction of the operating rod 3. At this time, since the operating rod 3 is extensible in the lengthwise direction of the operating rod 3, it can move together with the operating rod tilting mechanism 13 at two- or three-degree-of-freedom.

Further, the operating rod 3 has a limb supporting member 31 (described later) on its upper end. When a patient's limb is supported by the limb supporting member 31, the operating rod 3 can move the patient's limb. In another manner, the operating rod 3 can be moved by the patient's own will.

The training instructing unit 5 is fixed to the stationary frame 1 via a fixing member 7. The training instructing unit 5 executes a preset training program, and determines whether a first motion mode (described later) or a second motion mode is executed based on the training program. The first motion mode is a motion mode for operating the operating rod 3 based on a strength to be applied to the operating rod 3 by the patient. The second motion mode is a motion mode when the motion of the operating rod 3 is specified in the training program.

Further, the training instructing unit 5 provides a training route and an actual training motion of patient's limb according to the preset training program in a format of visual information or auditory information. As a result, the patient can feed back the training motion set by the training program and the actual motion and simultaneously train the limb. Further, the training instructing unit 5 may notify the user of arrival at a target tilting angle through the visual information or the auditory information also when the patient's limb can tilt the operating rod 3 to a target point (a target tilting angle) indicated by the training program. As a result, the patient's motivation for continuation of the training can be maintained.

As the training instructing unit 5, an integrated computer system that includes a display device such as a liquid crystal display, a CPU (Central Processing Unit), storage devices such as a RAM (Random Access Memory), a ROM (Read Only Memory), a hard disc, and an SSD (Solid State Disk), and an input device such as a touch panel as needed can be used. Further, the training instructing unit 5 may be configured so that the display device is separated from the other computer system. In this case, the display device is fixed to the stationary frame 1 via the fixing member 7.

The training program that is executed in the training instructing unit 5 has five training modes, for example, (i) a Guided Mode, (ii) an Initiated Mode, (iii) a Step Initiated Mode, (iv) a Follow Assist Mode, and (v) a Free Mode. The Guided Mode is the training mode in which the operating rod 3 moves a patient's limb to a predetermined direction at a constant speed regardless of motions of the limb. The Initiated Mode is the training mode for detecting a power with which the patient tries to move the operating rod 3 from an initial motion position to a proper direction through the limb with respect to the training route preset by the training program (referred to also as a haptic trigger), and causing the operating rod 3 to move the patient's limb to a direction of the predetermined training route at a constant speed. The Step Initiated Mode is the training mode for causing the operating rod 3 to move the patient's limb by a constant distance in the training route when the haptic trigger is detected on a predetermined portion in the training route of the operating rod 3. The Follow Assist Mode is the training mode for detecting the haptic trigger with every predetermined period and changing a speed of the operating rod 3 according to a magnitude of the detected haptic trigger. The Free Mode is the training mode for operating the operating rod 3 following the motion of the patient's limb.

The Free Mode in the five training modes is included in the first motion mode. On the other hand, the other training modes are included in the second motion mode. That is, the first motion mode is the motion mode for determining the motion direction and/or motion speed of the operating rod 3 based on a motion of the patient's limb (that is, the strength applied to the operating rod 3 by the patient's limb). On the other hand, in the second motion mode, the strength is detected in an initial motion, but a main motion of the operating rod 3 (the motion direction/motion speed) is instructed based on a training instruction specified in the training program.

The training apparatus 100 may further include a chair 9 on which the patient sits during the training. The chair 9 is connected to the stationary frame 1 via a chair connecting member 91, so that stability of the training apparatus 100 can be secured. Further, the chair connecting member 91 is fixed with good reproducibility so that the patient can conduct the training in a consistent position each time.

(2) Configurations of Controller and Operating Rod Tilting Mechanism

I. Entire Configuration

Figure 2:
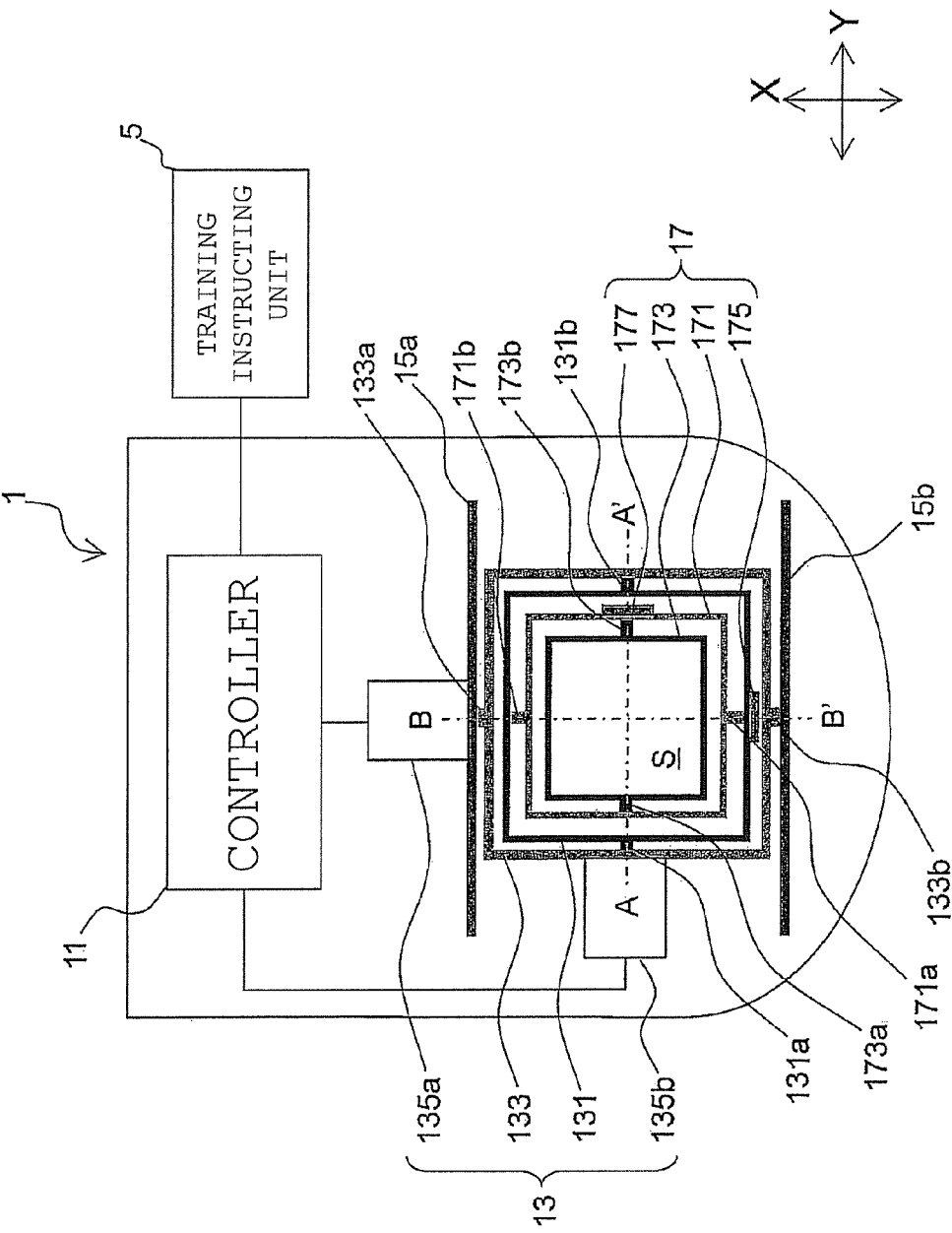
FIG. 2 is a diagram illustrating an entire configuration of a controller and an operating rod tilting mechanism in a stationary frame.

An entire configuration of a controller 11 and the operating rod tilting mechanism 13 are described below with reference to FIG. 2. FIG. 2 is a diagram illustrating the entire configuration of the controller and the operating rod tilting mechanism in the stationary frame. The controller 11 and the operating rod tilting mechanism 13 are disposed in the stationary frame 1. The controller 11 can receive a first motion mode executing instruction for executing the first motion mode or a second motion mode executing instruction for executing the second motion mode from the training instructing unit 5.

The controller 11 calculates a first motor control command (described later) for operating the operating rod 3 based on the strength applied to the operating rod 3 by the patient or the like in execution of the first motion mode (at the time of receiving the first motion mode executing instruction). On the other hand, the controller 11 calculates a second motor control command based on the training instruction of the operating rod at the time of executing the second motion mode (at the time of receiving the second motion mode executing instruction).

Further, the controller 11 is electrically connected to an X-axis tilting motor 135b (described later), a Y-axis tilting motor 135a (described later), and an expansion motor 359 (FIG. 5), and can supply driving powers to these motors, respectively. The controller 11, therefore, adjusts the driving powers to be output based on the first motor control command or the second motor control command so as to be capable of controlling these motors.

Figure 3:
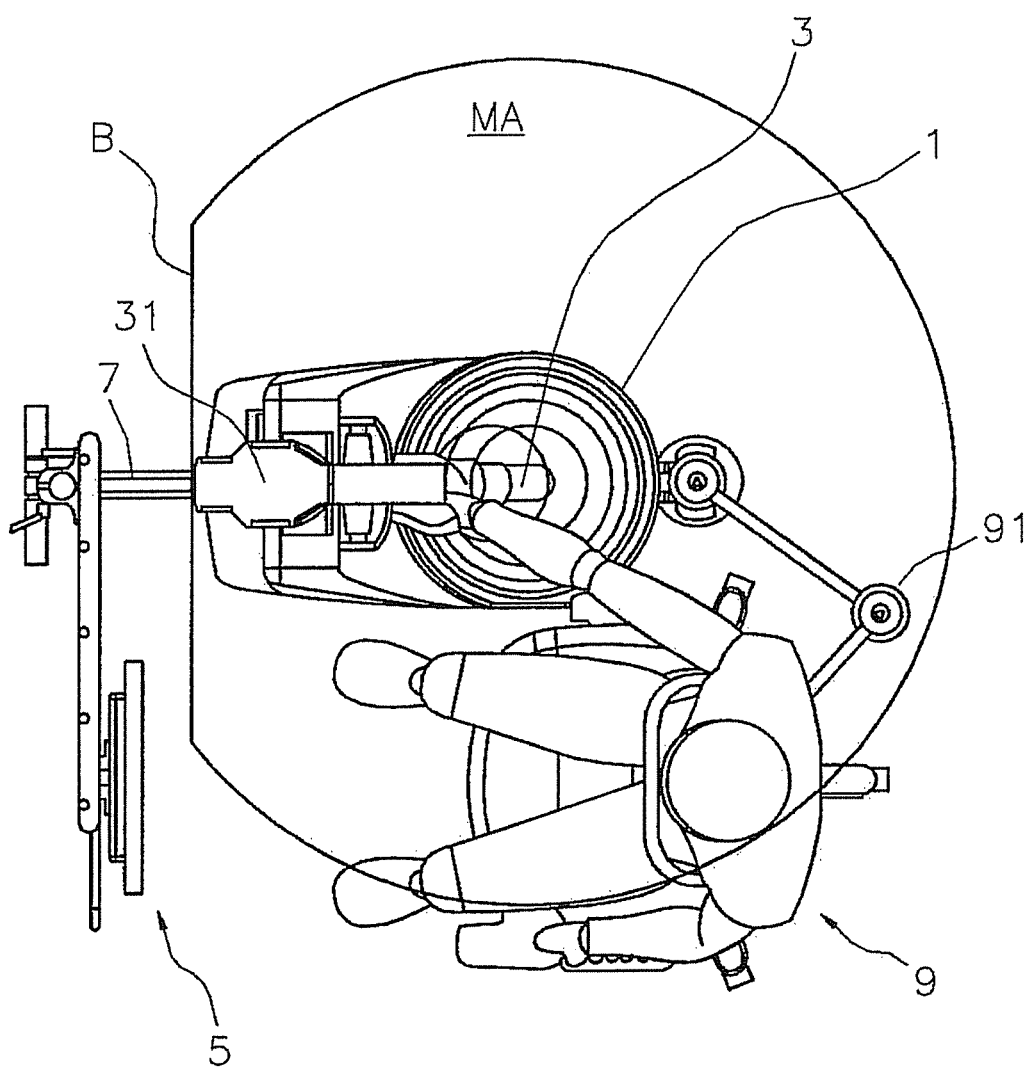
FIG. 3 is a diagram schematically illustrating an operating rod mobile region.

Further, the controller 11 defines an operating rod mobile region MA for defining a range where the operating rod 3 is movable as illustrated in FIG. 3. FIG. 3 is a diagram schematically illustrating the operating rod mobile region MA. In this embodiment, the operating rod mobile region MA is a region within a circle with a radius r about a position where the operating rod 3 is present (a motion position reference point O (described later)) when the operating rod 3 does not tilt, and this region is defined so that the operating rod 3 can move (tilt) within a range smaller than the radius r in a forward direction of the X-axis direction (in FIG. 3, a direction where the training instructing unit 5 is installed). Further, on the operating rod mobile region MA, a mobile region boundary line B for defining a boundary line of the operating rod mobile region MA is defined.

In this embodiment, the controller 11 controls the motors according to whether the motion position of the operating rod 3 is the radius r or less (in the forward direction of the X-axis direction, a predetermined value smaller than the radius r or less), or the radius r or more (in the forward direction of the X-axis direction, a predetermined value smaller than the radius r or more) so that the operating rod 3 makes a predetermined motion. As a result, the controller 11 can operate the operating rod 3 in a range where the patient does not feel a pain.

The operating rod mobile region MA can be a region having any shape other than the circular shape. Further, the operating rod mobile region MA may be expressed as a function on an X-Y-Z coordinate (an inequality expressing the region), or may be defined by some coordinate points for determining a boundary of the operating rod mobile region MA. Further, the radius, the function and/or the coordinate value that defines the operating rod mobile region MA may be stored in a storage device of a microcomputer system (described later) configuring the controller 11.

In this embodiment, the operating rod mobile region MA is realized by software. However, the operating rod mobile region MA is not limited to this, and may be mechanically realized by using a switch or the like. The detailed configuration and operation of the controller 11 are described later.

The operating rod tilting mechanism 13 is mounted to the stationary frame 1 via operating rod tilting mechanism fixing members 15a and 15b fixed to the stationary frame 1 so as to be capable of tilting. For this reason, the operating rod tilting mechanism 13 can operate (tilt) to the Y-axis direction (described later) with respect to the stationary frame 1. A configuration of the operating rod tilting mechanism 13 is described in detail below.

II. Configuration of Operating Rod Tilting Mechanism

The configuration of the operating rod tilting mechanism 13 according to this embodiment is described with reference to FIG. 2. The operating rod tilting mechanism 13 can tilt the operating rod 3 in the X-axis direction and the Y-axis direction using a "gimbal" mechanism that enables tilting on two axes. The X-axis direction is a vertical direction parallel with the X-axis in the vertical direction of FIG. 2. The Y-axis direction is a horizontal direction parallel with the Y-axis in the horizontal direction of FIG. 2.

The operating rod tilting mechanism 13 has an X-axis tilting member 131, a Y-axis tilting member 133, the X-axis tilting motor 135b and the Y-axis tilting motor 135a corresponding to the tilting members 131 and 133, respectively, and a strength detecting mechanism 17 (FIG. 2, and FIG. 4A to FIG. 43).

The X-axis tilting member 131 is disposed inside a space of the Y-axis tilting member 133 (described later). Further, the X-axis tilting member 131 has two axes 131a and 131b extending outside from two side surfaces having a normal line parallel with the Y axis. The two axes 131a and 131b are supported to two side surfaces having the normal line parallel with the Y axis of the Y-axis tilting member 133, respectively, so that the X-axis tilting member 131 can turn about the Y axis.

On the other hand, the Y-axis tilting member 133 has two axes 133a and 133b that extend outside from the two side surfaces having a normal line parallel with the X axis. The two axes 133a and 133b are supported to operating rod tilting mechanism fixing members 15a and 15b, respectively, so that the Y-axis tilting member 133 can turn about the X axis.

The X-axis tilting member 131 can tilt in the X-axis direction with respect to the Y-axis tilting member 133 and the Y-axis tilting member 133 can tilt in the Y-axis direction with respect to the operating rod tilting mechanism fixing members 15a and 15b, such that the operating rod tilting mechanism 13 can operate (tilt) at two-dimensional (occasionally one-dimensional) degree of freedom with respect to the stationary frame 1.

In FIG. 2, the X-axis tilting member 131 is disposed inside the space of the Y-axis tilting member 133. However, a design may be changed such that the X-axis tilting member 131 is disposed outside the space of the Y-axis tilting member 133 and a corresponding member can tilt.

The Y-axis tilting motor 135a is fixed to the operating rod tilting mechanism fixing member 15a. Further, an output rotational shaft of the Y-axis tilting motor 135a is connected to the axis 133a extended from the Y-axis tilting member 133 via a deceleration mechanism, not illustrated, so as to be capable of turning about the axis 133a.

The X-axis tilting motor 135b is fixed to a side surface that pivotally supports the axis 131a extending from the X-axis tilting member 131. Further, an output rotational shaft of the X-axis tilting motor 135b is connected to the axis 131a extended from the X-axis tilting member 131 via the deceleration mechanism, not illustrated, so as to be capable of turning about the axis 131a.

The Y-axis tilting motor 135a and the X-axis tilting motor 135b are controlled by the supply of the driving powers from the controller 11. Therefore, the Y-axis tilting motor 135a and the X-axis tilting motor 135b can tilt the operating rod 3 in the Y-axis direction and the X-axis direction at 2-degree-of-freedom based on the driving powers calculated by a motor control command.

Electric motors such as servomotors or brushless motors can be used as the Y-axis tilting motor 135a and the X-axis tilting motor 135b.

When the operating rod tilting mechanism 13 tilts the operating rod 3 at 1-degree-of-freedom, the operating rod tilting mechanism 13 needs to include only the X-axis tilting member 131 and the X-axis tilting motor 135b, or the Y-axis tilting member 133 and the Y-axis tilting motor 135a. In another manner, even when the operating rod tilting mechanism 13 includes the above two members and two motors, a combination of any member and any motor is disabled so that the operating rod tilting mechanism 13 can tilt the operating rod 3 at 1-degree-of-freedom.

A strength detecting mechanism 17 detects the power (strength) applied to the operating rod 3 as a tilt angle of the strength detecting mechanism 17 with respect to the X-axis tilting member 131. The strength detecting mechanism 17, then, converts the detected tilt angle into an electric signal (the strength component signal (described later)) so as to output the electric signal. A configuration of the strength detecting mechanism 17 is described in detail below.

III. Configuration of Strength Detecting Mechanism

Figure 4A:
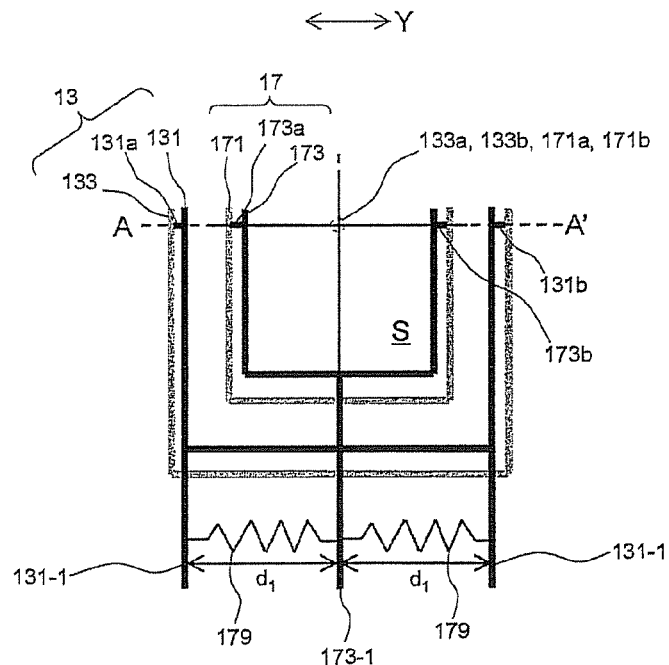
FIG. 4A is a sectional view taken along plane A-A' of the operating rod tilting mechanism and a strength detecting mechanism.

The detailed configuration of the strength detecting mechanism 17 is described with reference to FIG. 2 and FIG. 4A. FIG. 4A is a sectional view of the operating rod tilting mechanism 13 and the strength detecting mechanism 17 on a plane A-A'. As illustrated in FIG. 2, the strength detecting mechanism 17 can tilt the operating rod 3 in the X-axis direction and the Y-axis direction through the "gimbal" mechanism that enables the motions on the two axes similarly to the operating rod tilting mechanism 13. For this reason, the strength detecting mechanism 17 has a Y-axis strength detecting member 171, an X-axis strength detecting member 173, an Y-axis strength detector 175, an X-axis strength detector 177, and an energizing member 179.

The Y-axis strength detecting member 171 has two axes 171a and 171b extending to an outside from the two side surfaces having the normal line parallel with the X axis, respectively. The two axes 171a and 171b are supported to the X-axis tilting member 131 so as to be capable of turning about the X axis. The X-axis strength detecting member 173 has two axes 173a and 173b extending to an outside from the two side surfaces having the normal line parallel with the Y axis. The two axes 173a and 173b are supported to the Y-axis strength detecting member 171 so as to be capable of turning about the Y axis.

The Y-axis strength detecting member 171 is supported to the X-axis tilting member 131 so as to be capable of turning about the X axis and the X-axis strength detecting member 173 is supported to the Y-axis strength detecting member 171 so as to be capable of turning about the Y axis, so that the strength detecting mechanism 17 can tilt in the X-axis direction and the Y-axis direction with respect to the operating rod tilting mechanism 13.

The Y-axis strength detector 175 has a rotatable axis (rotational shaft), and outputs a signal (the strength component signal) based on a rotation amount of the rotational axis. The Y-axis strength detector 175 is fixed to the X-axis tilting member 131 so that the rotational axis matches the axis 171a or 171b of the Y-axis strength detecting member 171. The X-axis strength detector 177 has a rotatable axis (a rotational axis), and outputs a signal (the strength component signal) based on the rotation amount of the rotational axis. The X-axis strength detector 177 is fixed to the Y-axis strength detecting member 171 so that the rotational axis matches the axis 173a or 173b of the X-axis strength detecting member 173.

With the above configuration, the Y-axis strength detector 175 and the X-axis strength detector 177 can detect a tilt angle of the Y-axis strength detecting member 171 with respect to the X-axis tilting member 131 and a tilt angle of the X-axis strength detecting member 173 with respect to the Y-axis strength detecting member 171.

The tilt angle of the Y-axis strength detecting member 171 with respect to the X-axis tilting member 131 corresponds to a tilt angle of the strength detecting mechanism 17 in the Y-axis direction with respect to the operating rod tilting mechanism 13. Further, the tilt angle of the X-axis strength detecting member 173 with respect to the Y-axis strength detecting member 171 corresponds to a tilt angle of the strength detecting mechanism 17 in the X-axis direction with respect to the operating rod tilting mechanism 13.

As the Y-axis strength detector 175 and the X-axis strength detector 177, for example, potentiometers for detecting an axial rotation can be used. Potentiometers for detecting the axial rotation may include, for example, reference electrodes and measurement electrodes, wherein reference voltages (or reference currents) are applied between the reference electrodes. In this state, when a rotational axis of each potentiometer rotates, a voltage according to a rotation amount of the axis of each potentiometer is generated on the measurement electrodes. That is, each potentiometer can detect the tilt angle of the strength detecting mechanism 17 with respect to the operating rod tilting mechanism as a voltage change.

The energizing member 179 includes, for example, a plurality of circular-spiral leaf springs. As illustrated in FIG. 4A, a connecting end provided to a center of the spring spiral configuring the energizing member 179 is fixed to an energizing member fixing section 173-1 provided to a center of the X-axis strength detecting member 173. Further, a connecting end provided to an outermost peripheral portion of the spiral spring configuring the energizing member 179 is fixed to an energizing member fixing section 131-1 provided to the X-axis tilting member 131.

The X-axis tilting member 131 and the X-axis strength detecting member 173 are connected via the energizing member 179, so that the strength detecting mechanism 17 can follow the tilting of the operating rod tilting mechanism 13 and tilt.

Further, the operating rod 3 is inserted into a space S provided in the X-axis strength detecting member 173, and is fixed to the X-axis strength detecting member 173. As a result, the operating rod 3 follows the tilt of the operating rod tilting mechanism 13 so as to be capable of operating (tilting) at 2-degree-of-freedom via the strength detecting mechanism 17.

Figure 4B:
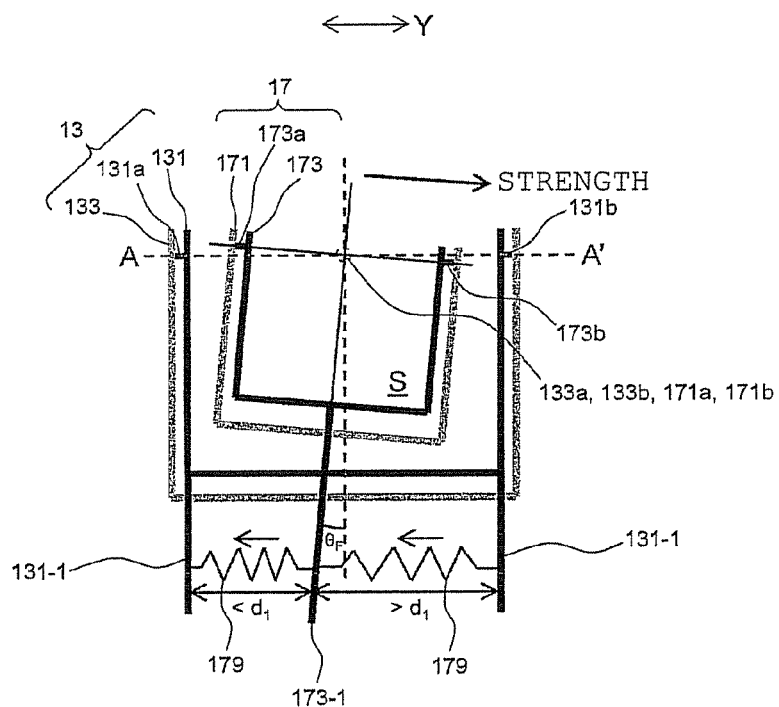
FIG. 4B is a diagram illustrating a relationship between the operating rod tilting mechanism and the strength detecting mechanism when a force is applied to an operating rod.

A principle such that the strength detecting mechanism 17 having the above configuration detects the strength to be applied to the operating rod 3 is described. As illustrated in FIG. 4B, for example, a force of a right direction in the Y-axis direction on a paper is applied to the operating rod 3. FIG. 4B is a diagram illustrating a relationship between the operating rod tilting mechanism and the strength detecting mechanism when the force is applied to the operating rod.

When the force of the Y-axis direction is applied to the operating rod 3, the Y-axis strength detecting member 171 and the X-axis strength detecting member 173 tilt in the Y-axis direction with respect to the X-axis tilting member 131 according to the force, so that the energizing member 179 is deformed. Specifically, when a radius of the energizing member 179 when the force is not applied to the operating rod 3 is denoted as $d_1$, a left portion of the energizing member 179 on the paper with respect to the energizing member fixing section 173-1 is compressed by the energizing member fixing section 173-1 of the X-axis strength detecting member 173, so that a length of the energizing member 179 becomes shorter than the radius $d_1$. On the other hand, a right portion on the paper with respect to the energizing member fixing section 173-1 is extended by the energizing member fixing section 173-1 of the X-axis strength detecting member 173, and thus the length becomes larger than the radius $d_1$.

Due to the deformation of the energizing member 179, the Y-axis strength detecting member 171 of the strength detecting mechanism 17 is displaced in a clockwise direction by a tilt angle $\theta_F$ with respect to the X-axis tilting member 131 of the operating rod tilting mechanism 13. When the strength to be applied to the operating rod 3 is balanced with the energizing force caused by the deformation of the energizing member 179, the tilt angle $\theta_F$ obtains a constant value.

Therefore, the tilt angle $\theta_F$ (a rotation amount of the axis 171a) is detected as a voltage signal by the Y-axis strength detector 175, so that a strength component in the Y-axis direction applied to the operating rod 3 can be output as the strength component signal.

On the other hand, when the force in the X-axis direction is applied to the operating rod 3, the X-axis strength detecting member 173 tilts with respect to the Y-axis strength detecting member 171 so that the biasing force caused by the deformation of the energizing member 179 is balanced with the force in the X-axis direction, and thus tilts with respect to the X-axis tilting member 131. When the force in the X-axis direction is applied to the operating rod 3, the Y-axis strength detecting member 171 does not change the tilt angle with respect to the X-axis tilting member 131. This is because the Y-axis strength detecting member 171 is pivotally supported to the X-axis tilting member 131 so as to be capable of turning about the X axis.

Therefore, the tilt angle of the X-axis strength detecting member 173 with respect to the Y-axis strength detecting member 171 when the force is applied in the X-axis direction becomes the tilt angle of the X-axis strength detecting member 173 with respect to the X-axis tilting member 131. Therefore, the tilt angle of the X-axis strength detecting member 173 with respect to the Y-axis strength detecting member 171 is detected by the X-axis strength detector 177, so that a strength component in the X-axis direction can be measured as the strength component signal.

An actual strength component can be calculated from the strength component signal based on a relationship between a deformation magnitude of the energizing member 179 and the strength to be applied to the operating rod 3. The deformation magnitude of the energizing member 179 and the strength to be applied to the operating rod 3 generally establish a proportional relationship, but not limited to the proportional relationship, and can establish any relationship according to characteristics of the energizing member 179.

Further, when the strength that is not parallel with the X-axis direction or the Y-axis direction is applied to the operating rod 3, the Y-axis strength detector 175 and the X-axis strength detector 177 detect a Y-axis component (the Y-axis strength component) and an X-axis component (the X-axis strength component) of the strength applied to the operating rod 3, respectively. The Y-axis strength detector 175 and the X-axis strength detector 177 output the strength component signals based on magnitudes of the detected strength components. Since the strength detecting mechanism 17 has the two strength detectors, the strength detecting mechanism 17 can detect the strength in any direction on the X-Y plane.

(3) Configuration of Operating Rod
I. Entire Configuration

Figure 5:
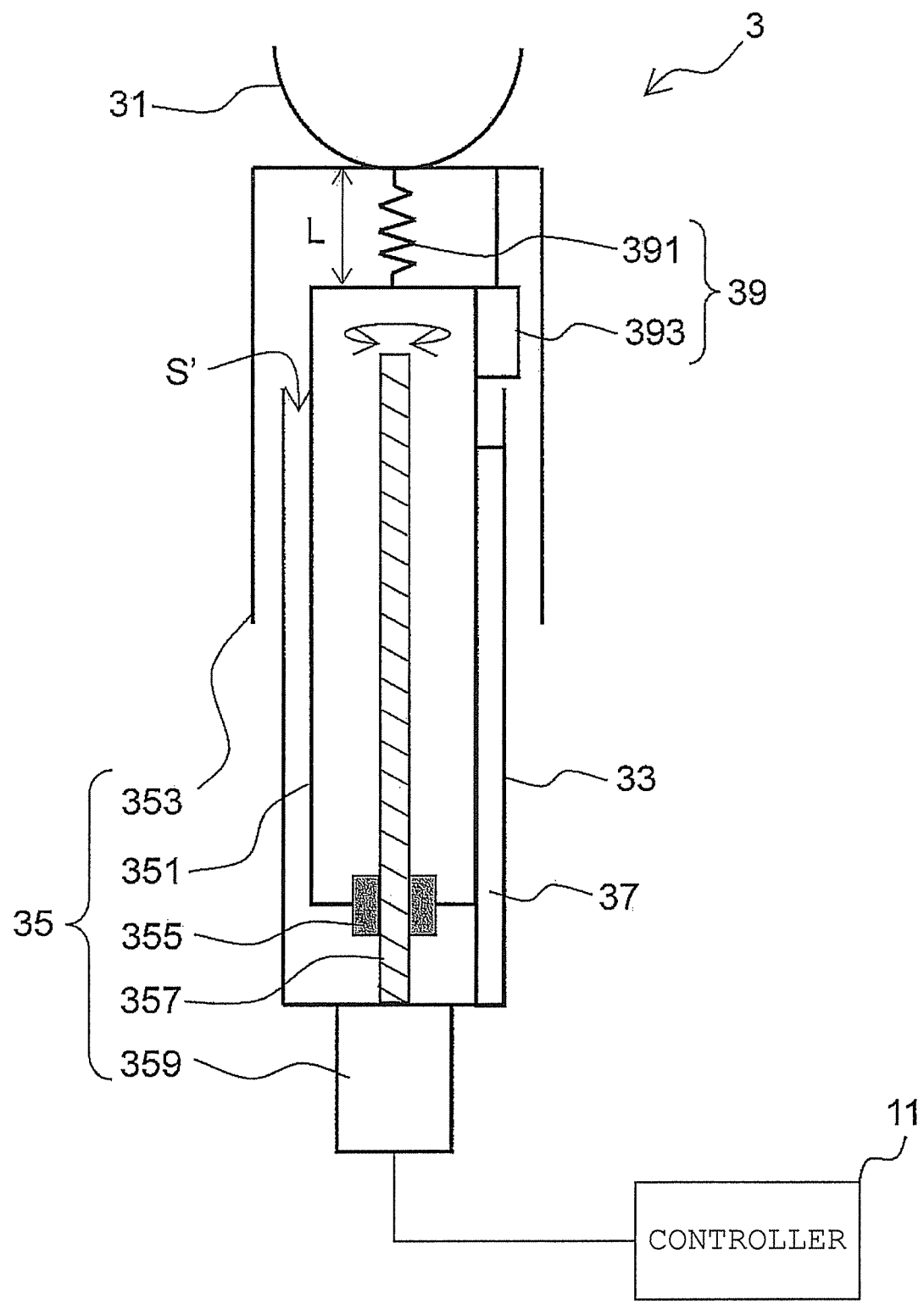
FIG. 5 is a diagram illustrating a configuration of the operating rod.

The configuration of the operating rod 3 is described below with reference to FIG. 5. The entire configuration of the operating rod 3 is described first. FIG. 5 is a diagram illustrating the configuration of the operating rod. The operating rod 3 includes a limb supporting member 31, a fixing stay 33, an expansion mechanism 35, and a lengthwise strength detecting mechanism 39. The limb supporting member 31 is fixed to an upper end of a cover 353 (described later) of the expansion mechanism 35. The limb supporting member 31 supports a patient's limb.

The fixing stay 33 forms a main body of the operating rod 3. Further, the fixing stay 33 has a space S' where a movable stay 351 (described later) of the expansion mechanism 35 is housed. Further, the fixing stay 33 is fixed to an operating rod fixing section of the X-axis strength detecting member 173.

The expansion mechanism 35 is provided to the fixing stay 33 so as to be movable along a lengthwise direction of the fixing stay 33. As a result, the operating rod 3 is extensible along the lengthwise direction of the operating rod 3. A configuration of the expansion mechanism 35 is described in detail later.

The lengthwise strength detecting mechanism 39 detects a strength applied in the lengthwise direction of the operating rod 3 by a patient's limb. Specifically, a lengthwise strength detector 393 (in this embodiment, a linear motion potentiometer) detects an extended length ΔL of the energizing member 391 (for example, a spring) one end of which is fixed to the cover 353 and the other end of which is fixed to the movable stay 351, and the lengthwise strength detecting mechanism 39 detects the strength in the lengthwise direction.

When the lengthwise strength detector 393 includes the linear motion potentiometer, the lengthwise strength component signal expressing the strength component in the lengthwise direction is obtained as an output voltage from the linear motion potentiometer that changes according to the extended length ΔL of the energizing member 391.

II. Configuration of Expansion Mechanism

The configuration of the expansion mechanism 35 is described below with reference to FIG. 5. The expansion mechanism 35 has the movable stay 351, the cover 353, a nut 355, a screw shaft 357, and the expansion motor 359. The movable stay 351 is inserted into the space S' provided in the fixing stay 33. Further, the movable stay 351 has a slide unit that is slidably engaged with a guide rail 37 provided to an inner wall of the fixing stay 33. The cover 353 is fixed to an upper end of the movable stay 351 via the energizing member 391 of the lengthwise strength detecting mechanism 39. Further, the cover 353 has the limb supporting member 31 at an upper end.

The nut 355 is mounted to a bottom portion of the movable stay 351. The screw shaft 357 (described later) is screwed into the nut 355. The screw shaft 357 is a member that extends parallel with the lengthwise direction of the fixing stay 33 and is provided with a screw thread.

The expansion motor 359 is fixed to the bottom portion of the fixing stay 33. Further, an output rotational shaft of the expansion motor 359 is connected to one end of the screw shaft 357 in the lengthwise direction so as to be rotatable about the screw shaft 357. Further, the expansion motor 359 is electrically connected to the controller 11. The expansion motor 359 is, therefore, driven by the driving power output from the controller 11. Since the expansion mechanism 35 has the above configuration, the screw shaft 357 is rotated about the axis by the expansion motor 359 so that the movable stay 351 is movable along the lengthwise direction of the fixing stay 33.

(4) Configuration of Controller
I. Entire Configuration

Figure 6:
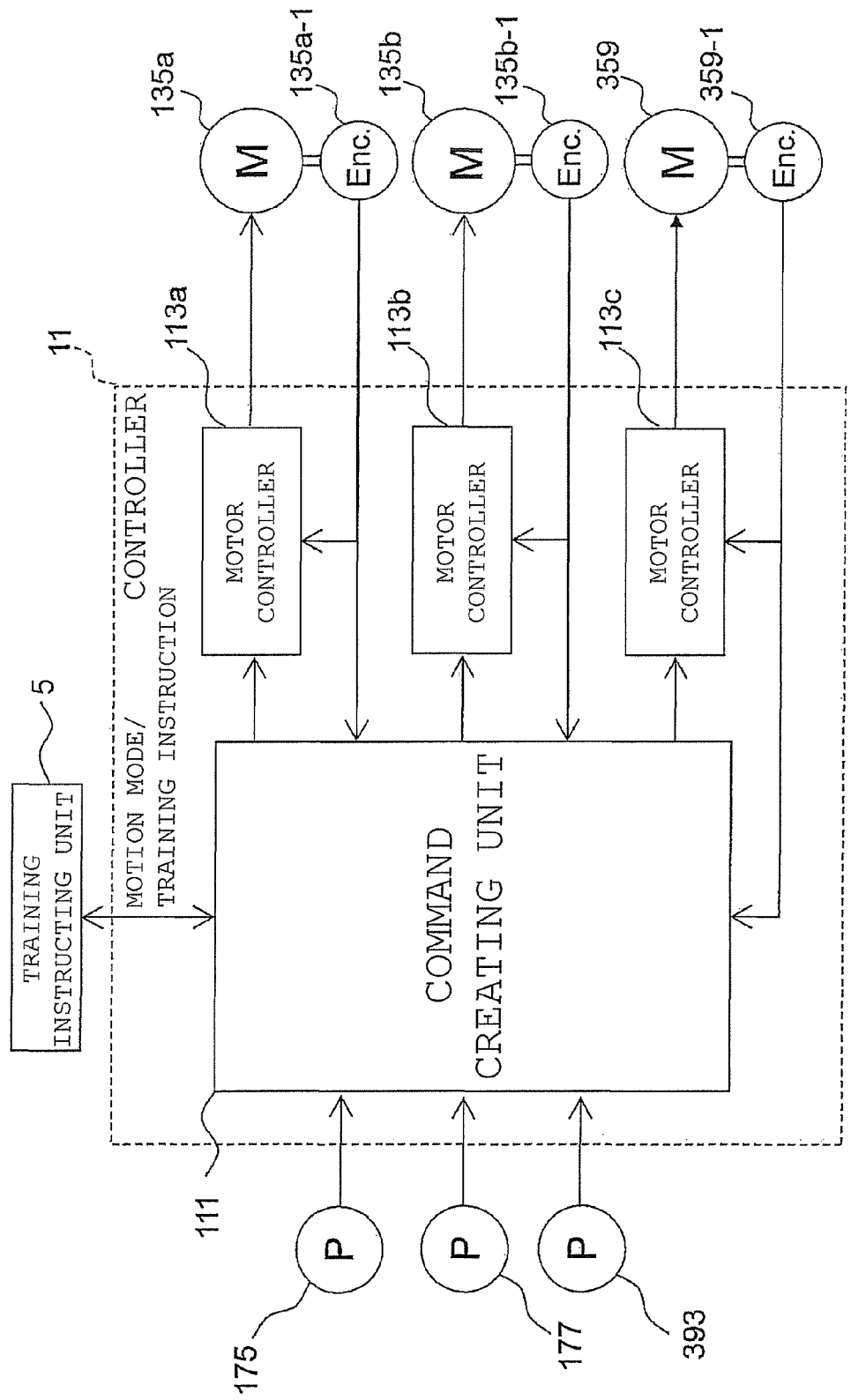
FIG. 6 is a diagram illustrating an entire configuration of the controller.

An entire configuration of the controller 11 is described below with reference to FIG. 6. FIG. 6 is a diagram illustrating the entire configuration of the controller. As the controller 11, a microcomputer system having, for example, a CPU, a storage device such as a RAM, a ROM, a hard disc device, or an SSD, and an interface for converting an electric signal can be used. Some or all of functions of the controller 11 described below may be realized as programs that can be executed in the microcomputer system. The programs may be stored in the storage device of the microcomputer system. Further, some or all of the functions of the controller 11 may be realized by a custom IC. The controller 11 has a command creating unit 111, and motor controllers 113a, 113b and 113c.

The command creating unit 111 can input a Y-axis strength component signal representing the strength component in the Y-axis direction, an X-axis strength component signal representing the strength component in the X-axis direction, and a lengthwise strength component signal representing a strength component in the lengthwise direction of the operating rod 3 from the Y-axis strength detector 175, the X-axis strength detector 177, and the lengthwise strength detector 393, respectively. Further, the command creating unit 111 can input signals from a first motion position detector 135*a*-1, a second motion position detector 135*b*-1, and a third motion position detector 359-1.

The motion position detectors are fixed to the output rotational shaft of the Y-axis tilting motor 135*a*, the output rotational shaft of the X-axis tilting motor 135*b*, and the output rotational shaft of the expansion motor 359, respectively, and output rotation amounts of the output rotational shafts of the respective motors. That is, the motion position detectors detect motion positions in freedom degree directions where the operating rod 3 is movable, respectively.

Specifically, the first motion position detector 135*a*-1 detects the motion position (the tilt angle) of the operating rod 3 in the Y-axis direction based on the rotation amount of the Y-axis tilting motor 135*a*. The second motion position detector 135*b*-1 detects the motion position (the tilt angle) of the operating rod 3 in the X-axis direction based on the rotation amount of the X-axis tilting motor 135*b*. The third motion position detector 359-1 detects the motion position of the operating rod 3 in the lengthwise direction based on a rotation amount of the expansion motor 359.

Encoders such as incremental encoders or absolute encoders can be used suitably as the motion position detectors. The encoders output pulse signals according to the rotation amounts of the corresponding motors.

The command creating unit 111 can receive the first motion mode executing instruction or the second motion mode executing instruction from the training instructing unit 5, and outputs either the first motor control command (described later) or the second motor control command (described later) according to the received executing instructions. The configuration of the command creating unit 111 is described in detail later.

The motor controllers 113*a*, 113*b* and 113*c* can input the motor control commands from the command creating unit 111, respectively, and calculate the driving powers of the motors based on the input motor control commands. The motor controllers 113*a*, 113*b* and 113*c* supply the calculated driving powers to the Y-axis tilting motor 135*a*, the X-axis tilting motor 135*b*, and the expansion motor 359, respectively.

Further, the motor controllers 113*a*, 113*b* and 113*c* can input the rotation amounts of the corresponding motors from the first motion position detector 135*a*-1, the second motion position detector 135*b*-1, and the third motion position detector 359-1, respectively, and can control the motors in view of the rotation amounts of the motors. Therefore, for example, a motor control device using a feedback control theory can be used as the motor controllers 113*a*, 113*b* and 113*c*.

Since the controller 11 has the above configuration, the controller 11 can output a suitable motor control command (the first motor control command or the second motor control command) according to a motion mode executing instruction input from the training instructing unit 5 to control the motors. As a result, the operating rod 3 can suitably move according to the motion mode currently being executed.

II. Configuration of Command Creating Unit

Figure 7:
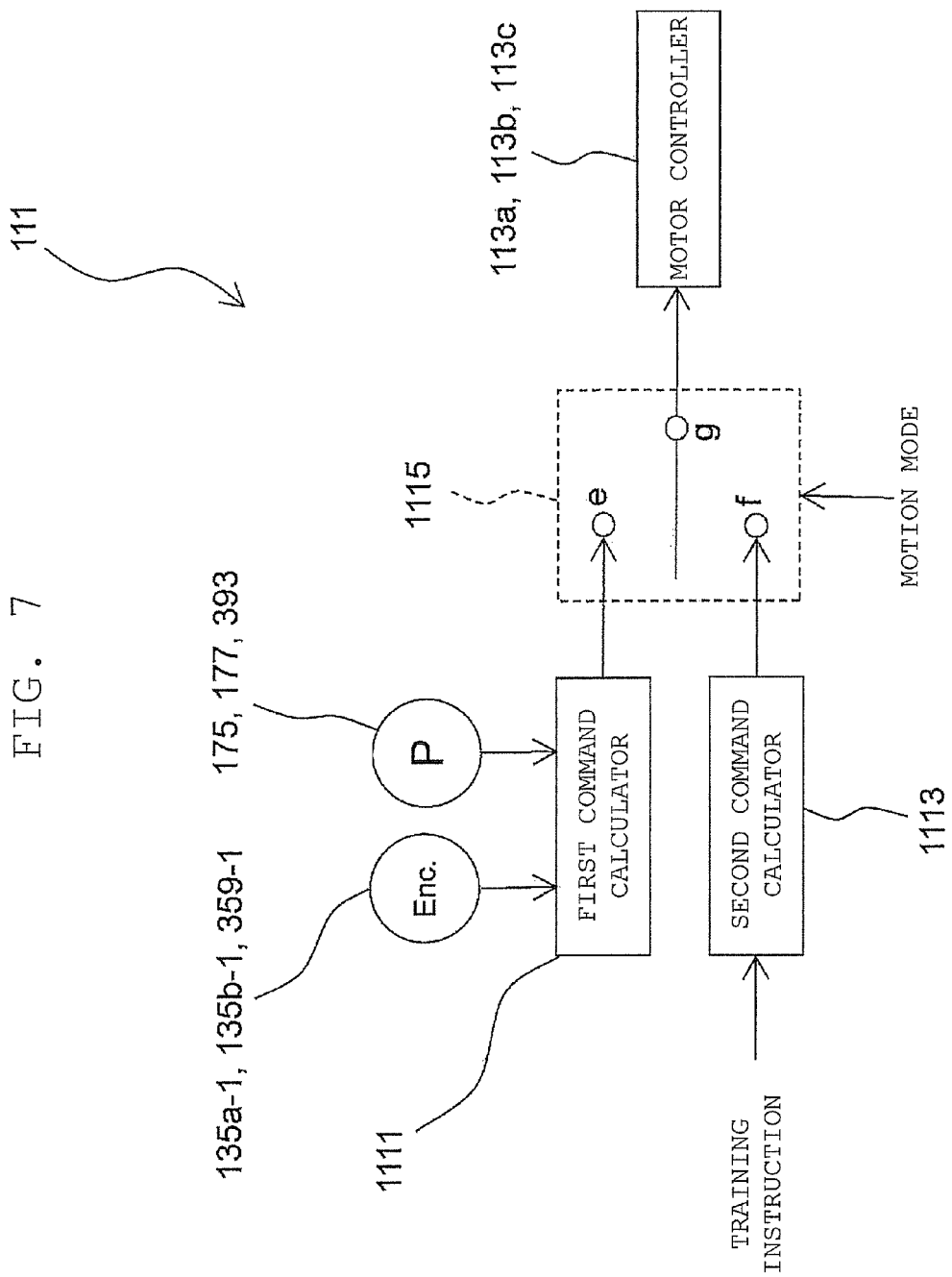
FIG. 7 is a diagram illustrating a configuration of a command creating unit.

The configuration of the command creating unit 111 is described below with reference to FIG. 7. FIG. 7 is a diagram illustrating the configuration of the command creating unit. The command creating unit 111 has a first command calculator 1111, a second command calculator 1113, and a control command switching unit 1115.

The first command calculator 1111 can input the strength component signal and the motion position of the operating rod 3 from each of the strength detectors and each of the motion position detectors. The first command calculator 1111 calculates the first motor control command based on the input strength component signal and/or the motion position of the operating rod 3. The configuration of the first command calculator 1111 is described in detail later.

The second command calculator 1113 can input a training instruction specified in the training program from the training instructing unit 5, and calculates the second motor control command based on the input training instruction.

The control command switching unit 1115 has two inputs e and f, and one output g. The first motor control command is input into the input e from the first command calculator 1111, and the second motor control command is input into the input f from the second command calculator 1113. Further, the output g is connected to the motor controllers 113*a*, 113*b* and 113*c*. When the control command switching unit 1115 receives the first motion mode executing instruction from the training instructing unit 5, the output g is connected to the input e. On the other hand, when the control command switching unit 1115 receives the second motion mode executing instruction from the training instructing unit 5, the output g is connected to the input f.

This configuration enables the command creating unit 111 to select and output the first motor control command to the motor controllers 113*a*, 113*b* and 113*c* when the first motion mode is executed, and to select and output the second motor control command to the motor controllers 113*a*, 113*b* and 113*c* when the second motion mode is executed. As a result, the respective motors are controlled by the suitable motor control command according to the motion mode currently being executed. As a result, the operating rod 3 can suitably move according to the motion mode currently being executed.

III. Configuration of First Command Calculator

Figure 8:
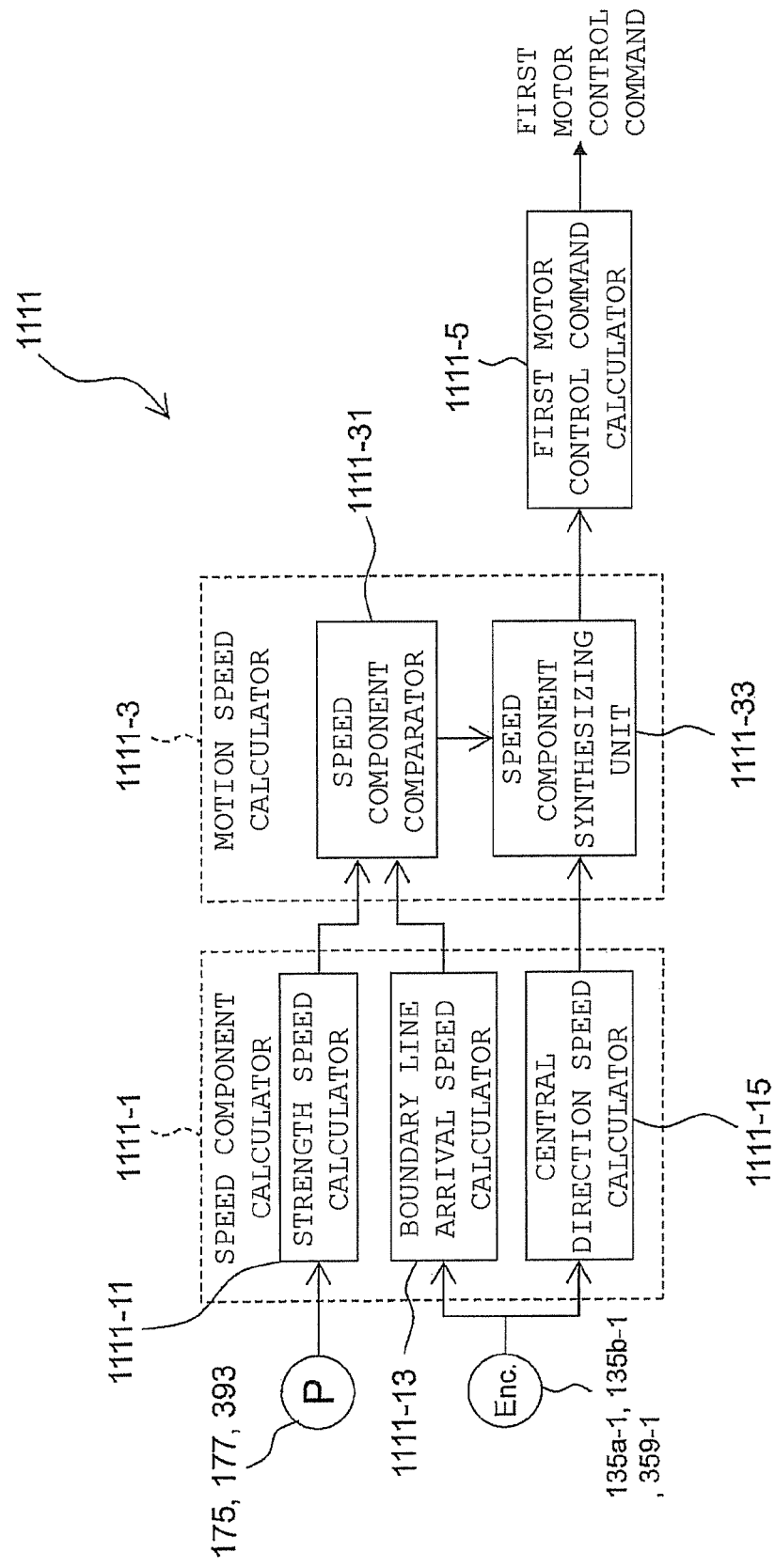
FIG. 8 is a diagram illustrating a configuration of a first command calculator of the training apparatus according to a first embodiment.

The configuration of the first command calculator 1111 is described below with reference to FIG. 8. FIG. 8 is a diagram illustrating the configuration of the first command calculator of the training apparatus according to the first embodiment. The first command calculator 1111 has a speed component calculator 1111-1, a motion speed calculator 1111-3, and a first motor control command calculator 1111-5.

The speed component calculator 1111-1 can input the strength component signals from the three strength detectors and the motion positions of the operating rod 3 from the three motion position detectors. The speed component calculator 1111-1 calculates a plurality of speed components with different characteristics based on the strength component signals and/or the motion positions of the operating rod 3. A configuration of the speed component calculator 1111-1, and the speed components calculated in this embodiment are described in detail later.

The motion speed calculator 1111-3 can input the plurality of speed components calculated by the speed component calculator 1111-1, and synthesizes the plurality of speed components based on a predetermined condition, so as to calculate the motion speed of the operating rod 3. The configuration of the motion speed calculator 1111-3 in this embodiment is described in detail below.

The first motor control command calculator 1111-5 can input the motion speed of the operating rod 3 from the motion speed calculator 1111-3, and calculates the first motor control command based on the input motion speed.

The above configuration enables the first command calculator 1111 to calculate the suitable motion speed of the operating rod 3 by using the plurality of speed components based on a predetermined condition, and to calculate the first motor control command based on the calculated motion speed.

IV. Configuration of Speed Component Calculator

The configuration of the speed component calculator 1111-1 according to this embodiment is described below with reference to FIG. 8. The speed component calculator 1111-1 has a strength speed calculator 1111-11, a boundary line arrival speed calculator 1111-13, and a central direction speed calculator 1111-15.

The strength speed calculator 1111-11 can input the strength component signals output from the three strength detectors, and calculates a strength speed of the operating rod 3 based on the strength component signals. In this embodiment, the strength speed is calculated as a speed that is linearly increased with respect to an increase in the strength applied to the operating rod 3. However, not limited to this, the strength speed may be calculated as any function with respect to the strength according to the motion of the operating rod 3.

The boundary line arrival speed calculator 1111-13 can input the motion positions of the operating rod 3 from the three motion position detectors. The boundary line arrival speed calculator 1111-13 calculates a boundary line arrival speed based on a distance from a current motion position of the operating rod 3 to the mobile region boundary line B of the operating rod mobile region MA illustrated in FIG. 3. The distance from the current motion position of the operating rod 3 to the mobile region boundary line B is referred to as "a boundary line distance".

The boundary line arrival speed calculator 1111-13 calculates a speed, whose absolute value becomes smaller as the boundary line distance is shorter, as the boundary line arrival speed. That is, the boundary line arrival speed calculator 1111-13 calculates the speed, at which the operating rod 3 is moved more slowly as the motion position of the operating rod 3 is closer to the mobile region boundary line B, as the boundary line arrival speed.

The central direction speed calculator 1111-15 inputs the motion positions of the operating rod 3 from the three motion position detectors, and when the current motion position of the operating rod 3 is out of the operating rod mobile region MA, the central direction speed calculator 1111-15 calculates a central direction speed.

The central direction speed is a speed component for causing the motion position of the operating rod 3 to be directed toward a reference point. That is, the central direction speed is a speed at which the operating rod 3 is moved to the reference point of the motion position. The reference point of the motion position of the operating rod 3 is occasionally referred to as "the motion position reference point O". In this embodiment, the motion position reference point O is a point at which the tilt angle (motion position) of the operating rod 3 is 0.

The above configuration enables the speed component calculator 1111-1 to calculate three kinds of speeds including the strength speed that linearly increases with respect to the increase in the strength, the boundary line arrival speed at which the operating rod 3 is moved more slowly as approaching the mobile region boundary line B, and the central direction speed directed to the motion position reference point as the speed components.

V. Configuration of Motion Speed Calculator

The configuration of the motion speed calculator 1111-3 according to this embodiment is described below with reference to FIG. 8. In this embodiment, the motion speed calculator 1111-3 has a speed component comparator 1111-31 and a speed component synthesizing unit 1111-33.

The speed component comparator 1111-31 can input the strength speed and the boundary line arrival speed from the speed component calculator 1111-1, and selects the one of the strength speed and the boundary line arrival speed that is lower (whose absolute value is lower) so as to output it.

The speed component synthesizing unit 1111-33 synthesizes the one of the strength speed and the boundary line arrival speed input from the speed component comparator 1111-31 with the central direction speed input from the speed component calculator 1111-1 so as to calculate the motion speed.

When calculating the motion speed, the speed component synthesizing unit 1111-33 synthesizes a maximum motion speed $V_{max}$ with the central direction speed when the absolute value of the input strength speed or boundary line arrival speed is larger than the maximum motion speed $V_{max}$, so as to obtain the motion speed. That is, the speed component synthesizing unit 1111-33 limits the motion speed of the operating rod 3 to the maximum motion speed $V_{max}$ or less.

In the above configuration, when the current motion position of the operating rod 3 is within the operating rod mobile region MA, the motion speed calculator 1111-3 outputs the one of the strength speed and the boundary line arrival speed that is lower (whose absolute value is lower) as the motion speed of the operating rod 3. On the other hand, when the motion position of the operating rod 3 is outside the operating rod mobile region MA, the motion speed calculator 1111-3 calculates the motion speed including the central direction speed.

As a result, when the operating rod 3 is near the mobile region boundary line B within the operating rod mobile region MA, the motion speed calculator 1111-3 can limit the motion speed of the operating rod 3 to a low speed. On the other hand, when the operating rod 3 is outside the operating rod mobile region MA, the motion speed calculator 1111-3 can calculate a speed of the direction in which the operating rod 3 returns to the operating rod mobile region MA.

As a result, when the operating rod 3 reaches the mobile region boundary line B within the operating rod mobile region MA, an abrupt stop of the operating rod 3 and an impact on a limb, or a movement of the operating rod 3 outside the operating rod mobile region MA due to inertia, can be restrained. Further, even if the operating rod 3 moves outside the operating rod mobile region MA, the operating rod 3 is returned into the operating rod mobile region MA.

(5) Operation of Training Apparatus

The operation of the training apparatus 100 according to this embodiment is described below. A method for calculating the boundary line arrival speed in the boundary line arrival speed calculator 1111-13 and a method for calculating the central direction speed in the central direction speed calculator 1111-15 are described.

I. Method for Calculating Boundary Line Arrival Speed

Figure 9:
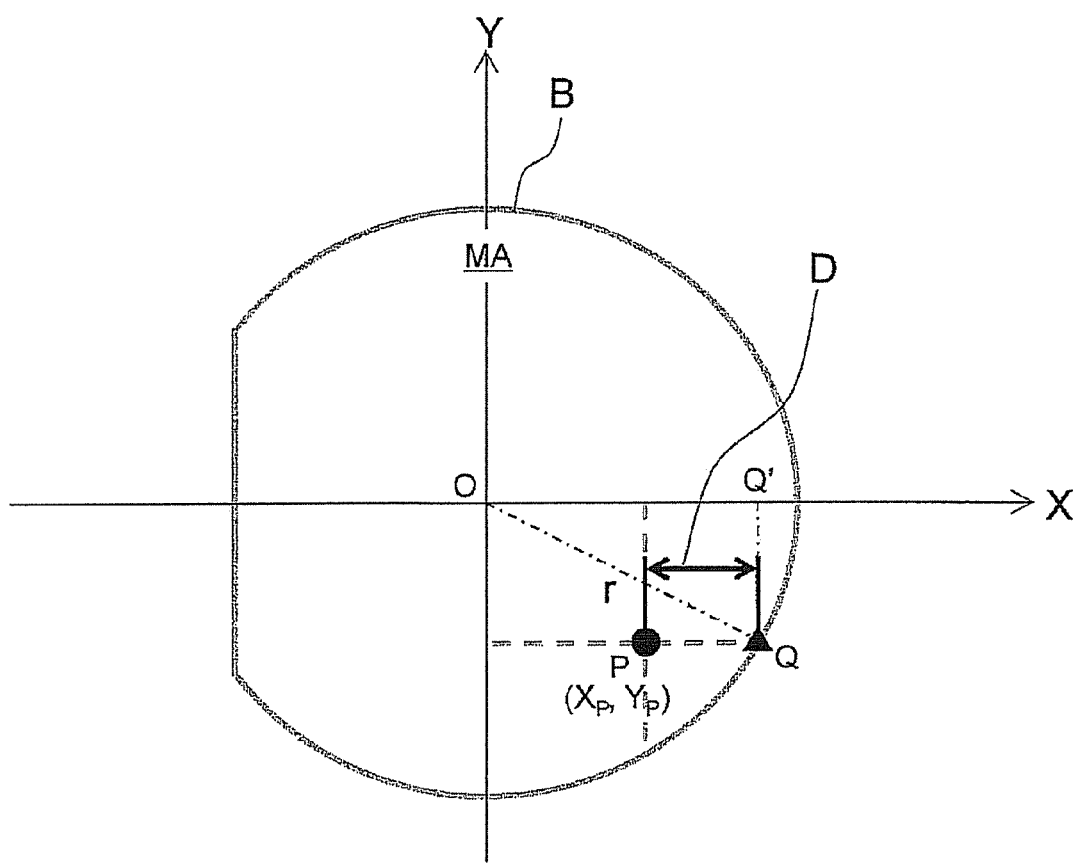
FIG. 9 is a diagram schematically illustrating a method for calculating a boundary line arrival speed.

The method for calculating the boundary line arrival speed in the boundary line arrival speed calculator 1111-13 is described with reference to FIG. 9. FIG. 9 is a diagram schematically illustrating the method for calculating the boundary line arrival speed. The description with reference to FIG. 9 refers to a method for calculating a component of the boundary line arrival speed in the X-axis direction as an example. The component of the boundary line arrival speed in the Y-axis direction can be calculated similarly. As to the component of the boundary line arrival speed in the lengthwise direction, the boundary line arrival speed can be calculated with a middle length between a minimum shortened length and a maximum extended length of the operating rod 3 being the motion position reference point in the lengthwise direction in an approximately similar manner as described below.

In order to calculate the boundary line arrival speed, the boundary line arrival speed calculator 1111-13 obtains the current motion position of the operating rod 3 from the motion position detector. The current motion position of the operating rod 3 is motion position P ($X_P$, $Y_P$).

The boundary line arrival speed calculator 1111-13 calculates a boundary line distance D from a current motion position P of the operating rod 3 to the mobile region boundary line B. In this embodiment, the boundary line distance D in the X-axis direction is a distance between an intersection Q between a straight line that passes through the current motion position P and is parallel with the X axis and the mobile region boundary line B, and an X coordinate value $X_P$ of the current motion position P.

The boundary line arrival speed calculator 1111-13 calculates a specific (X) coordinate value of the intersection Q in the following manner. As illustrated in FIG. 9, the Y coordinate value of the intersection Q is the same as the Y coordinate value $Y_P$ of the motion position P. On the other hand, it is found that the X coordinate value of the intersection Q corresponds to a length of a side OQ' of a triangle OQQ' formed by the motion position reference point O, the intersection Q, and an intersection Q' between a perpendicular line drawn from the intersection Q to the X axis and the X axis as illustrated in FIG. 9.

In this embodiment, the operating rod mobile region MA is defined as a region within a circle with the radius r excluding a predetermined region on a minus value side of the X axis (the operating rod mobile region MA is a ID-shaped region). Further, as illustrated in FIG. 9, a length of a side OQ of the triangle OQQ' matches the radius r of the operating rod mobile region MA. Therefore, in the triangle OQQ', the length of the side OQ' is calculated with the length of the side OQ being denoted as r and the length of the side QQ' being denoted as $Y_P$, so that an X coordinate value of the intersection Q can be calculated.

After the X coordinate value of the intersection Q is calculated, the boundary line arrival speed calculator 1111-13 calculates (an absolute value of) a difference between the X coordinate value of the intersection Q and the X coordinate value of the motion position P as the boundary line distance D in the X-axis direction.

The boundary line arrival speed calculator 1111-13 calculates a speed directed from the current motion position P toward the intersection Q as the X-axis component of the boundary line arrival speed using the calculated boundary line distance D. In this embodiment, the boundary line arrival speed calculator 1111-13 calculates (the X-axis component of) the boundary line arrival speed so that the operating rod moves from the motion position P toward the intersection Q while decelerating at a predetermined constant deceleration.

Figure 10:
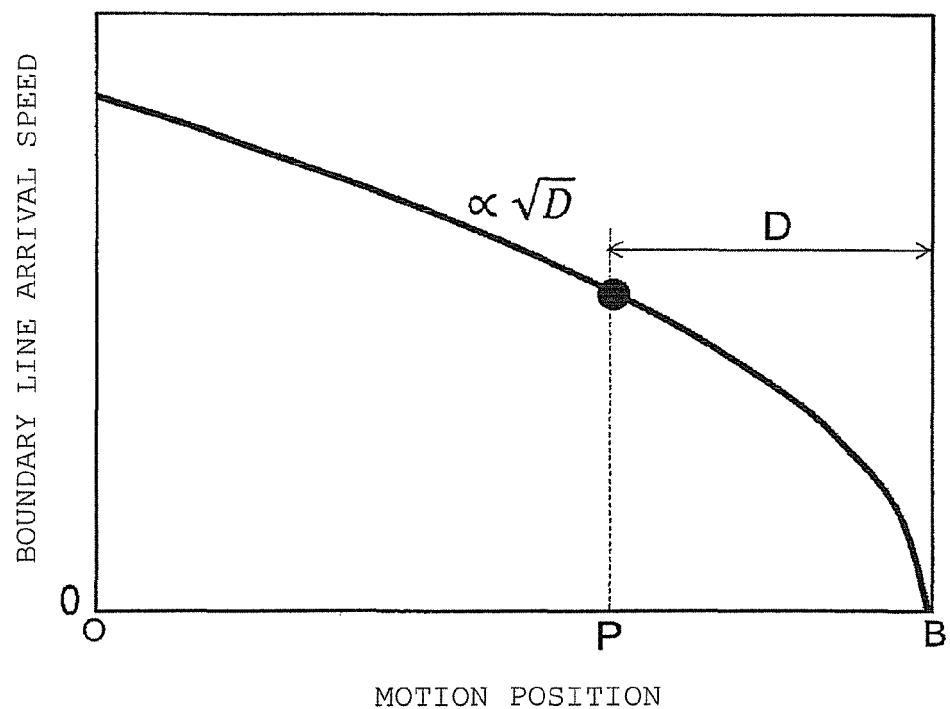
FIG. 10 is a diagram illustrating a relationship between a motion position of the operating rod and the boundary line arrival speed to be calculated.

When the boundary line arrival speed is calculated by using the above calculating method, the boundary line arrival speed illustrated in FIG. 10 can be calculated. FIG. 10 is a diagram illustrating a relationship between a motion position of the operating rod and the boundary line arrival speed to be calculated.

As illustrated in FIG. 10, the boundary line arrival speed calculated by using the above method is calculated as a speed whose magnitude (an absolute value) is smaller as the motion position of the operating rod 3 (a horizontal axis in FIG. 10) approaches the mobile region boundary line B (namely, the boundary line distance is shorter) within the operating rod mobile region MA.

In this embodiment, the boundary line arrival speed is calculated as a formula that is proportional to a square root of the boundary line distance D (the motion position of the operating rod 3). This is because the boundary line arrival speed approaches the mobile region boundary line B while decreasing at a constant deceleration in this region.

This is more clear also from a formula expressing a relationship among a distance, a speed, an acceleration and a time (since $D=at^2/2$ and $V=at$, $V=SQRT(2aD)$ (D: the distance, a: the acceleration, V: the speed, t: the time, SQRT (2aD): a square root of the value 2aD)).

Also when the current motion position P of the operating rod 3 is outside the operating rod mobile region MA, the boundary line arrival speed calculator 1111-13 can calculate the boundary line arrival speed in a direction toward the mobile region boundary line B similarly to the above.

II. Method for Calculating Central Direction Speed

Figure 11:
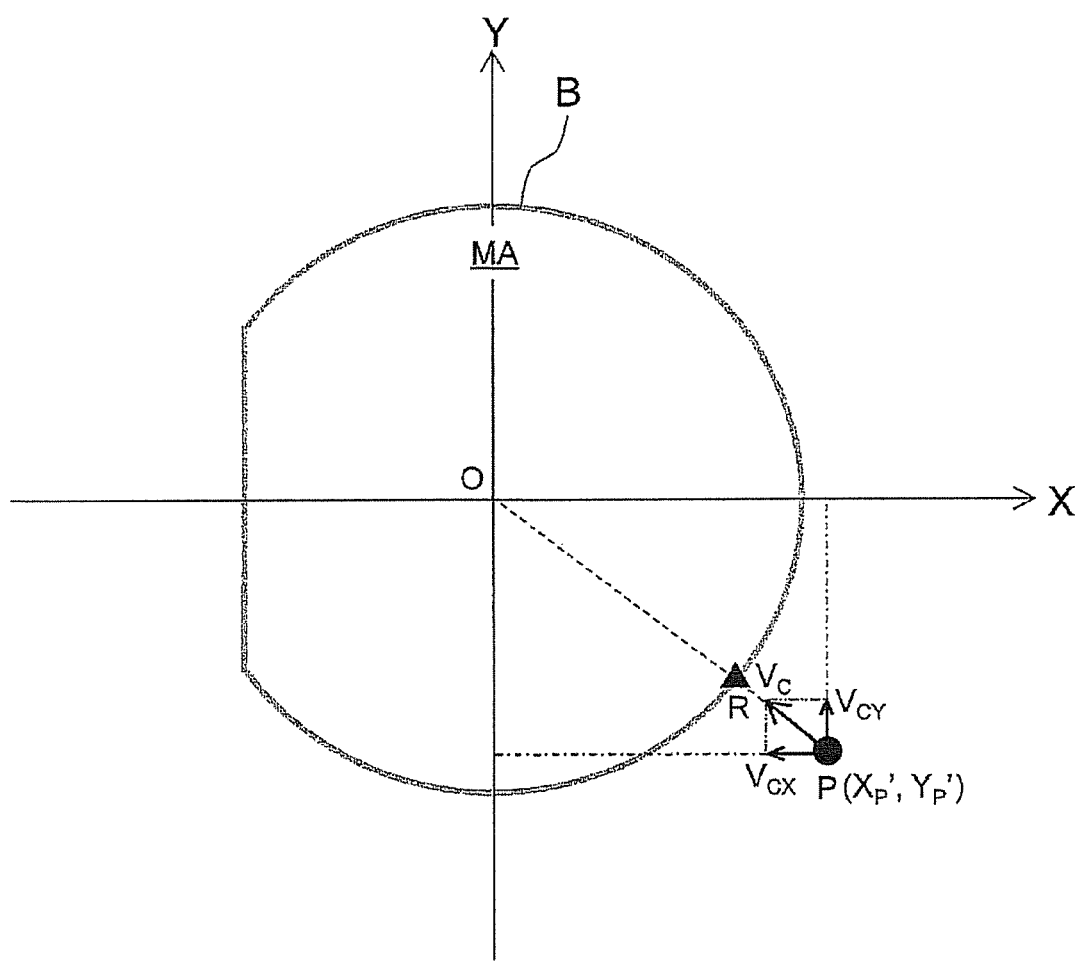
FIG. 11 is a diagram schematically illustrating a method for calculating a central direction speed.

The method for calculating the central direction speed in the central direction speed calculator 1111-15 according to this embodiment is described below with reference to FIG. 11. FIG. 11 is a diagram schematically illustrating the method for calculating the central direction speed. The central direction speed is calculated when the motion position P of the operating rod 3 is outside the operating rod mobile region MA as illustrated in FIG. 11. For this reason, the central direction speed calculator 1111-15 checks whether the current motion position P of the operating rod 3 is outside the operating rod mobile region MA. For example, in FIG. 11, a check is made whether the distance from the motion position reference point O to the motion position P is the radius r of the circle that defines the operating rod mobile region MA or more, so that the check can be made whether the motion position P is outside the operating rod mobile region MA.

When the determination is made that the current motion position P of the operating rod 3 is within the operating rod mobile region MA, the central direction speed calculator 1111-15 calculates the central direction speed as 0. On the other hand, when the determination is made that the current motion position P of the operating rod 3 is outside the operating rod mobile region MA, the central direction speed is calculated in the following manner.

The central direction speed calculator 1111-15 derives an intersection R between a straight line that passes through the motion position reference point O and the motion position P (coordinate: ($X_P'$, $Y_P'$)) and the mobile region boundary line B, and calculates a length of a line segment PR and a length of a line segment OP. Further, the central direction speed calculator 1111-15 calculates a magnitude of a central direction speed $V_C$ (scalar quantity) using the length of the line segment PR according to a formula for calculating the boundary line arrival speed (namely, a formula that is proportional to a square root of the length of the line segment PR)

After calculating the magnitude of the central direction speed $V_C$, the central direction speed calculator 1111-15 calculates the X-axis component $V_{CX}$ and the Y-axis component $V_{CY}$ of the central direction speed $V_C$. Specifically, the central direction speed calculator 1111-15 calculates a product of the magnitude of the central direction speed $V_C$ and a first component ratio as the X-axis component $V_{CX}$ of the central direction speed $V_C$. The first component ratio is a value of a ratio of an X coordinate value $X_P'$ of the motion position P to the length of the line segment OP. Further, the central direction speed calculator 1111-15 calculates a product of the magnitude of the central direction speed $V_C$ and a second component ratio as the Y-axis component $V_{CY}$ of the central direction speed V. The second component ratio is a value of a ratio of a Y coordinate value $Y_P{}'$ of the motion position P to the length of the line segment OP.

The X-axis component $V_{CX}$ and the Y-axis component $V_{CY}$ of the central direction speed $V_C$ are calculated as described above, the operating rod 3 is moved in the X-axis direction at the speed of the X-axis component $V_{CX}$ and is moved in the Y-axis direction at the speed of the Y-axis component $V_{CY}$. As a result, these speeds are synthesized, and the operating rod 3 moves from the current motion position P to the motion position reference point O as illustrated in FIG. 11. In other words, the central direction speed calculator 1111-15 calculates the X-axis component $V_{CX}$ and the Y-axis component $V_{CY}$ of the central direction speed $V_C$ as described above, so as to be capable of calculating the central direction speed $V_C$ (a vector amount) toward the motion position reference point O.

III. Operation of Training Apparatus (i) Basic Operation

Figure 12A:
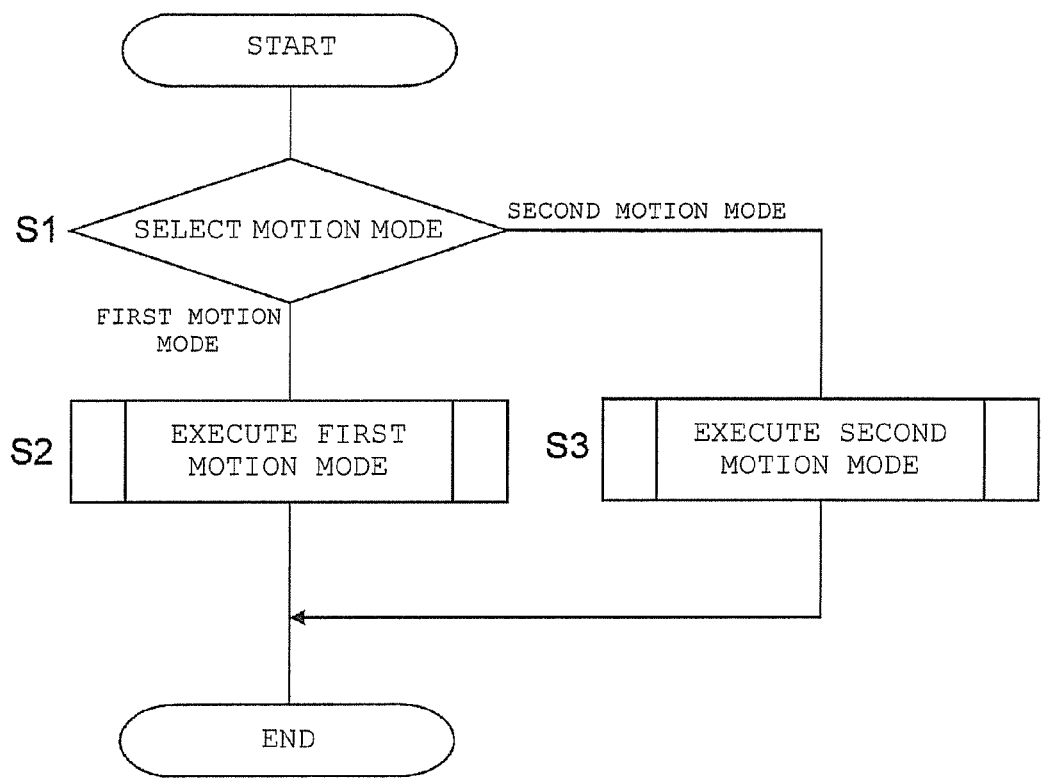
FIG. 12A is a flowchart illustrating a basic operation of the training apparatus.

A basic operation of the training apparatus 100 according to this embodiment is described below with reference to FIG. 12A. FIG. 12A is a flowchart illustrating the basic operation of the training apparatus.

When the operation of the training apparatus 100 starts, a selection is made whether the operating rod 3 is moved by the first motion mode or the operating rod 3 is moved by the second motion mode in the training instructing unit 5 (step S1).

Specifically, when the free mode is selected as the training program in the training instructing unit 5, the first motion mode for causing the operating rod 3 to move based on the strength applied to the operating rod 3 is selected as the motion mode. On the other hand, when a mode other than the free mode is selected as the training program in the training instructing unit 5, the second motion mode for causing the operating rod 3 to move based on a training instruction specified by the training program is selected as the motion mode.

After the motion mode is selected in the training instructing unit 5, the training instructing unit 5 transmits the first motion mode executing instruction to the controller 11 when the first motion mode is selected as the motion mode, and transmits the second motion mode executing instruction to the controller 11 when the second motion mode is selected as the motion mode.

When the first motion mode executing instruction is transmitted from the training instructing unit 5 ("the first motion mode" at step S1), the control command switching unit 1115 connects the input e to the output g. As a result, the first motor control command calculated by the first command calculator 1111 is output to the motor controllers 113a, 113b and 113c (step S2). That is, the first motion mode is executed in the training apparatus 100.

On the other hand, when the controller 11 receives the second motion mode executing instruction from the training instructing unit 5 ("the second motion mode" at step S1), the control command switching unit 1115 connects the input f to the output g. As a result, the second motor control command calculated by the second command calculator 1113 is output to the motor controllers 113a, 113b and 113c (step S3). That is, the second motion mode is executed in the training apparatus 100.

The motion mode is suitably selected according to the training program, and a motor control command (the first motor control command or the second motor control command) for controlling the operating rod 3 (motors 135a, 135b and 359) based on the selected motion mode (the first motion mode or the second motion mode) is selected, so that the training apparatus 100 can suitably operate the operating rod 3 according to the training program.

(ii) Operation of Training Apparatus in Execution of First Motion Mode

Figure 12B:
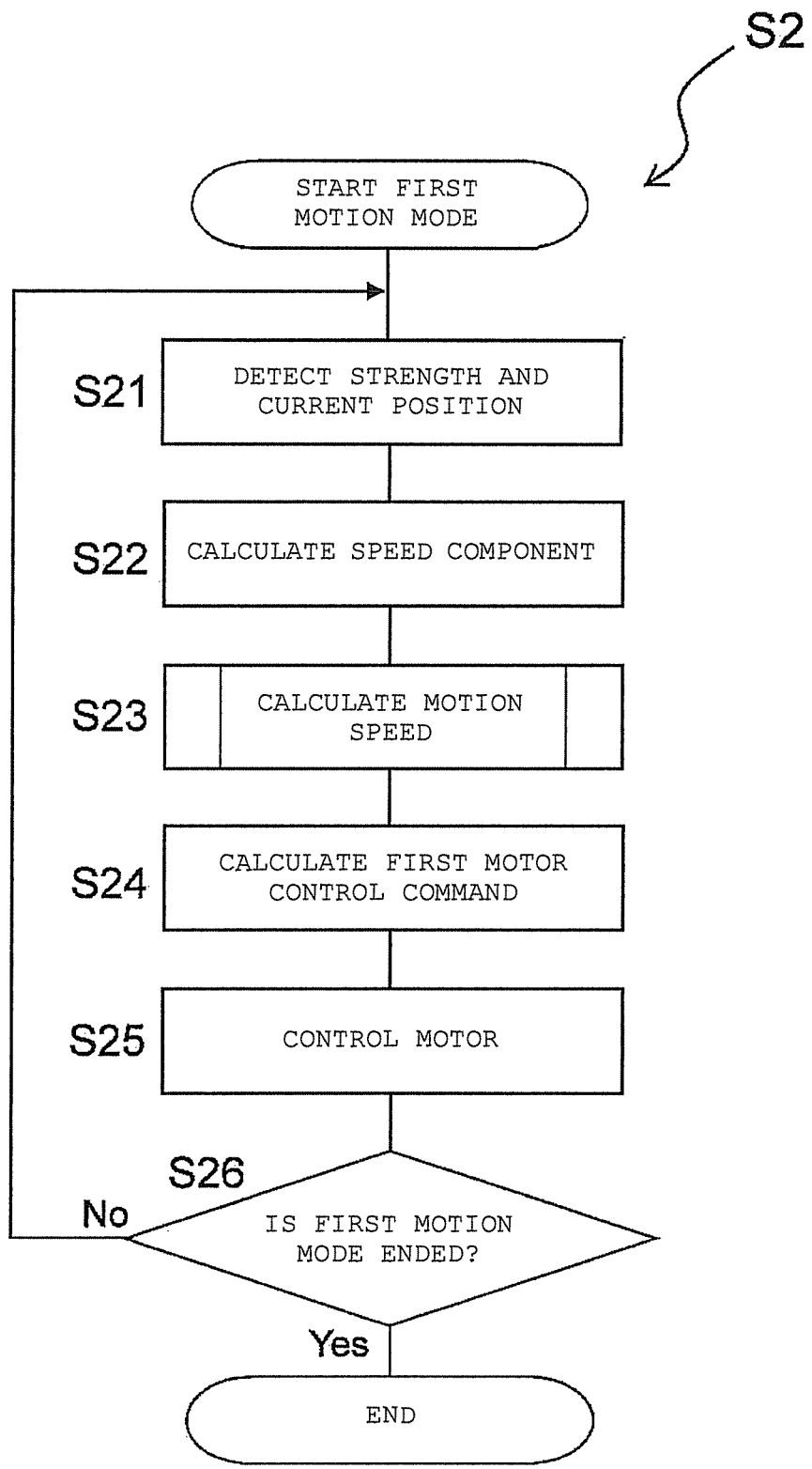
FIG. 12B is a flowchart illustrating a motion of a first motion mode.

The operation of the training apparatus 100 at the time of executing the first motion mode at step S2 is described below with reference to FIG. 12B. FIG. 12B is a flowchart illustrating the first motion mode. When the execution of the first motion mode is started, the first command calculator 1111 obtains the current motion positions of the operating rod 3 in the freedom degree directions from the three motion position detectors and the strength component signals (the strength components) in the freedom degree directions from the three strength detectors (step S21).

Thereafter, the speed component calculator 1111-1 calculates speed components using the current motion positions of the operating rod 3 and the strength component signals obtained at step S21 (step S22). Specifically, the strength speed calculator 1111-11 calculates the strength speed based on the strength component signals, and the boundary line arrival speed calculator 1111-13 calculates the boundary line arrival speed based on the current motion positions of the operating rod 3. Further the central direction speed calculator 1111-15 calculates the central direction speed. At this time, the speed component calculator 1111-1 calculates speed components corresponding to the freedom degree directions where the operating rod 3 is movable.

The motion speed calculator 1111-3 calculates the motion speed of the operating rod 3 using three speed components (the strength speed, the boundary line arrival speed, and the central direction speed) calculated at step S22 (step S23). A method for calculating the motion speed of the operating rod 3 at step S23 is described in detail later.

After the motion speed calculator 1111-3 calculates the motion speed of the operating rod 3, the first motor control command calculator 1111-5 calculates the first motor control command based on the motion speed of the operating rod 3 input from the motion speed calculator 1111-3 (step S24). At this time, the first motor control command calculator 1111-5 calculates the first motor control commands corresponding to the freedom degree directions where the operating rod 3 is movable.

After the first motor control command is calculated, the three motor controllers 113a, 113b and 113c input the corresponding first motor control commands for controlling the Y-axis tilting motor 135a, the X-axis tilting motor 135b, and the expansion motor 359, respectively. The three motor controllers output the driving powers for driving the motors to the corresponding motors, respectively, based on the corresponding first motor control commands. As a result, the three motors are controlled based on the first motor control commands (step S25).

The controller 11 checks whether the first motion mode is ended (step S26). Specifically, for example, when stop of the execution of the free mode is instructed by the training instructing unit 5, the controller 11 determines that the first motion mode is ended.

When the controller 11 determines that the first motion mode is ended ("Yes" at step S26), the controller 11 stops the control of the three motors so as to stop the execution of the first motion mode. On the other hand, when the controller 11 determines that the first motion mode is being executed (continued) (when "No" at step S26), the operation process of the training apparatus 100 returns to S21. That is, the controller 11 continues the control of the three motors. As a result, the controller 11 can continuously control the three motors during the execution of the first motion mode based on the first motor control command.

(iii) Method for Calculating Motion Speed of Operating Rod

Figure 12C:
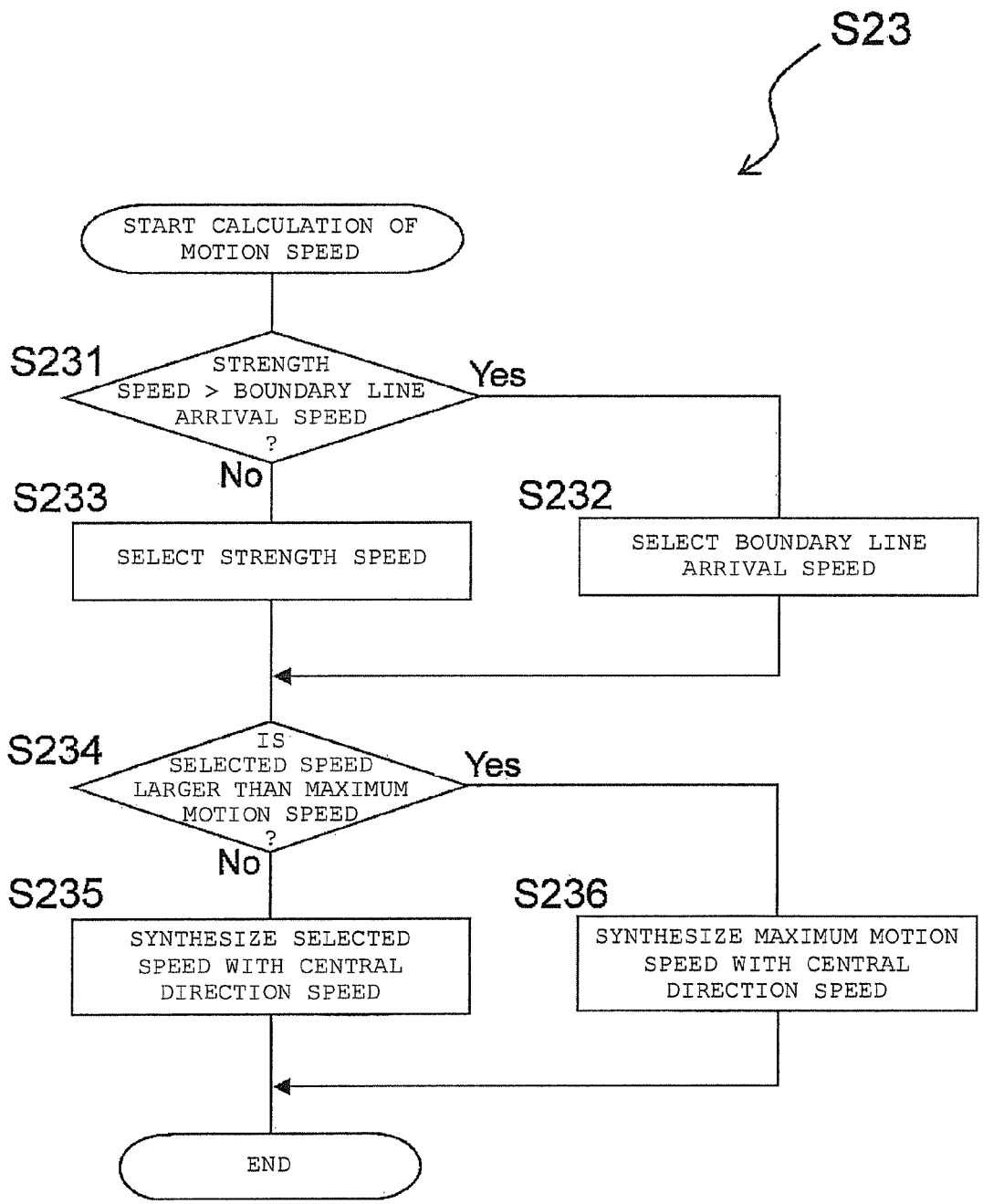
FIG. 12C is a flowchart illustrating a method for calculating a motion speed of the operating rod in the training apparatus according to the first embodiment.

The method for calculating the motion speed of the operating rod 3 at step S23 according to this embodiment is described below with reference to FIG. 12C. FIG. 12C is a flowchart illustrating the method for calculating the motion speed of the operating rod in the training apparatus according to the first embodiment. When the calculation of the motion speed of the operating rod 3 is started, the speed component comparator 1111-31 inputs the strength speed and the boundary line arrival speed from the speed component calculator 1111-1, and compares magnitudes (absolute values) of the strength speed and the boundary line arrival speed (step S231).

When the speed component comparator 1111-31 determines that the strength speed is higher than the boundary line arrival speed ("Yes" at step S231), the speed component comparator 1111-31 outputs the boundary line arrival speed to the speed component synthesizing unit 1111-33 (step S232). On the other hand, when the strength speed is determined as being the boundary line arrival speed or less ("No" at step S231), the speed component comparator 1111-31 outputs the strength speed to the speed component synthesizing unit 1111-33 (step S233).

The speed component synthesizing unit 1111-33 checks whether the absolute value of the input strength speed or the boundary line arrival speed is larger than the maximum motion speed $V_{max}$ (step S234). When the absolute value of the strength speed or the boundary line arrival speed is larger than the maximum motion speed $V_{max}$ ("Yes" at step S234), the speed component synthesizing unit 1111-33 selects the maximum motion speed $V_{max}$ as a speed to be synthesized with the central direction speed. The speed component synthesizing unit 1111-33 synthesizes the maximum motion speed $V_{max}$ with the central direction speed so as to calculate the motion speed, and outputs the calculated motion speed to the first motor control command calculator 1111-5 (step S236). Thereafter, the calculation of the motion speed is ended.

On the other hand, when the absolute value of the strength speed or the boundary line arrival speed is the maximum motion speed $V_{max}$ or less ("No" at step S234), the speed component synthesizing unit 1111-33 selects the strength speed or the boundary line arrival speed as a speed to be synthesized with the central direction speed. The speed component synthesizing unit 1111-33 synthesizes the speed selected from the strength speed or the boundary line arrival speed by executing steps S231 to S233 with the central direction speed so as to calculate the motion speed, and outputs the calculated motion speed to the first motor control command calculator 1111-5 (step S235). Thereafter, the calculation of the motion speed is ended.

Figure 13:
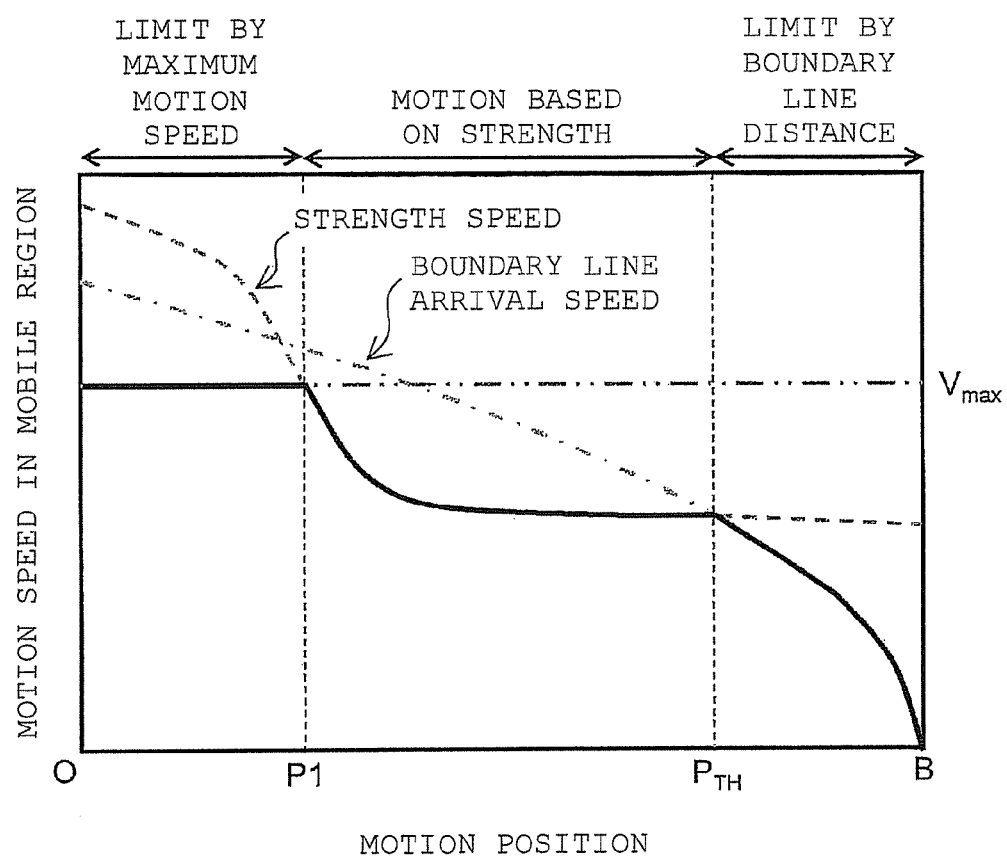
FIG. 13 is a diagram illustrating a relationship between the motion speed and the motion position of the operating rod in the operating rod mobile region.

How the speed to be synthesized with the central direction speed by executing steps S231 to S236 changes within the operating rod mobile region MA is described with reference to FIG. 13. FIG. 13 is a diagram illustrating a relationship between the motion speed and the motion position of the operating rod in the operating rod mobile region MA.

An example where a force is applied to the operating rod 3 and the operating rod 3 is moved from the motion position reference point O to the mobile region boundary line B is considered. In this example, as a result of applying the force to the operating rod 3, the strength speed illustrated by a dotted line in FIG. 13 is calculated. In FIG. 13, the calculated boundary line arrival speed is indicated by an alternate long and short dash line, the maximum motion speed $V_{max}$ is indicated by an alternate long and two short dashes line, and the actual motion speed of the operating rod 3 in the operating rod mobile region MA is indicated by a solid line.

As illustrated in FIG. 13, both the strength speed and the boundary line arrival speed are calculated as values larger than the maximum motion speed $V_{max}$ between the motion position reference point O and a motion position P1. In such a case, the motion speed of the operating rod 3 is limited to the maximum motion speed $V_{max}$. In this embodiment, even when the strength speed and/or the boundary line arrival speed are/is calculated as the value larger than the maximum motion speed $V_{max}$, the motion speed of the operating rod 3 is limited to the maximum motion speed $V_{max}$ or less.

After the motion position P1, (the absolute value of) the strength speed is lower than (the absolute value of) the boundary line arrival speed and lower than the maximum motion speed $V_{max}$. Therefore, the strength speed is output as the motion speed of the operating rod 3. That is, after the motion position P1, the operating rod 3 is moved based on the force (strength) applied to the operating rod 3.

Further, (the absolute value of) the boundary line arrival speed is lower than (the absolute value of) the strength speed and lower than the maximum motion speed $V_{max}$ in a range from a motion position $P_{TH}$ to the mobile region boundary line B. For this reason, in the motion position range, the operating rod 3 moves at the boundary line arrival speed. That is, the motion speed of the operating rod 3 is limited by the boundary line distance D (limited by the boundary line arrival speed) near the mobile region boundary line B.

When the force (strength) to be applied to the operating rod 3 is reduced and the calculated strength speed is lower than the boundary line arrival speed in the range from the motion position $P_{TH}$ to the mobile region boundary line B, the strength speed is selected as the motion speed of the operating rod 3. Therefore, the boundary line arrival speed can be said to set an upper limit value of the motion speed near the mobile region boundary line B.

As described above, particularly when the current motion position P of the operating rod 3 is near the mobile region boundary line B, the motion speed of the operating rod 3 is limited by the boundary line distance D. As a result, even when the force (strength) to be applied to the operating rod 3 is strong, the abrupt stop of the operating rod 3 on the mobile region boundary line B can be suppressed. As a result, when the operating rod 3 arrives at the mobile region boundary line B, an impact to be exerted on a limb by the operating rod 3 can be reduced.

Further, when the motion speed of the operating rod 3 is limited by the boundary line distance D, the operating rod 3 can be restrained from approaching the mobile region boundary line B at a high speed and exceeding the mobile region boundary line B due to inertia to move outside the operating rod mobile region MA.

Further, the speed to be synthesized with the central direction speed (the motion speed within the operating rod mobile region MA) is selected based on a magnitude relationship between the calculated value of the strength speed, the calculated value of the boundary line arrival speed, and the maximum motion speed $V_{max}$ (as described above, a minimum value of these speeds is selected). As a result, the operating rod 3 is prevented from operating at an excessively high speed, and the motion speed of the operating rod 3 is prevented from abruptly changing. For this reason, when the motion speed is switched, the impact to be exerted on the limb by the operating rod 3 can be reduced.

Further, when the current motion position of the operating rod 3 is outside the operating rod mobile region MA at step S235 or S236, the speed component selected at steps S231 to S234 is synthesized with the central direction speed that is not 0. As a result, the operating rod 3 is quickly returned to the operating rod mobile region MA.

In the operation of the training apparatus 100 according to the first embodiment described above, the respective steps of the operation may be changed and/or an executing order of the steps may be changed within the scope of the present invention.

2. Second Embodiment (1) Configuration of Training Apparatus According to Second Embodiment The training apparatus 100 according to the first embodiment calculates the motion speed obtained by synthesizing the lowest speed component selected from the strength speed, the boundary line arrival speed, and the maximum motion speed $V_{max}$ with the central direction speed. For this reason, in the training apparatus 100 according to the first embodiment, the motion speed is calculated so that the motion speed of the operating rod 3 becomes lower toward the mobile region boundary line B and the operating rod 3 stops on the mobile region boundary line B. The motion speed is, however, not limited to this. In a training apparatus 200 according to a second embodiment described below, when the operating rod 3 is near a mobile region boundary line B or on the mobile region boundary line B, the operating rod 3 is not stopped but the operating rod 3 is moved along the mobile region boundary line B depending on a strength applied to an operating rod 3.

In the training apparatus 200 according to the second embodiment, configurations of a speed component calculator 1111-1' and a motion speed calculator 1111-3' of a first command calculator 1111 are different from the configurations of the speed component calculator 1111-1 and the motion speed calculator 1111-3 of the training apparatus 100 according to the first embodiment. In the following description, therefore, only the configuration of the speed component calculator 1111-1' and the configuration of the motion speed calculator 1111-3' according to the second embodiment are described, and description of the other configurations is omitted.

I. Configuration of Speed Component Calculator

The configuration of the speed component calculator 1111-1' of the training apparatus 200 according to the second embodiment is described with reference to FIG. 14A. FIG. 14A is a diagram illustrating a configuration of the speed component calculator of the training apparatus according to the second embodiment. The speed component calculator 1111-1' of the training apparatus 200 according to the second embodiment includes a strength speed calculator 1111-11', a boundary line arrival speed calculator 1111-13', a central direction speed calculator 1111-15', a boundary direction speed calculator 1111-17', and a motion position predicting unit 1111-19'.

Since configurations and functions of the strength speed calculator 1111-11', the boundary line arrival speed calculator 1111-13', and the central direction speed calculator 1111-15' of the training apparatus 200 according to the second embodiment are the same as the configurations and functions of the strength speed calculator 1111-11, the boundary line arrival speed calculator 1111-13, and the central direction speed calculator 1111-15 according to the first embodiment, description thereof is omitted.

The boundary direction speed calculator 1111-17' calculates a boundary direction speed. The boundary direction speed is a speed component along the mobile region boundary line B. The boundary direction speed calculator 1111-17' inputs a predicted motion position P''' (described later) from the motion position predicting unit 1111-19' (described later) and the motion positions of the operating rod 3 from three motion position detectors, and calculates the boundary direction speed based on the input predicted motion position P''' and a current motion position P of the operating rod 3. A method for calculating the boundary direction speed in the boundary direction speed calculator 1111-17' is described in detail later.

The motion position predicting unit 1111-19' inputs strength component signals of corresponding freedom degree directions from three strength detectors 175, 177, and 393, and synthesizes the input strength component signals so as to calculate a resultant strength. The resultant strength, therefore, corresponds to the strength applied to the operating rod 3 obtained by synthesizing detected strength components in the respective freedom degree directions (the X-axis direction, a Y-axis direction, and a lengthwise direction). That is, the motion position predicting unit 1111-19' calculates the resultant strength (the strength applied to the operating rod 3) as a vector quantity, namely, a resultant strength vector F.

Further, the motion position predicting unit 1111-19' inputs the motion positions of the operating rod 3 from the three motion position detectors, and calculates the predicted motion position P''' based on the resultant strength and the input current motion positions P of the operating rod 3.

The predicted motion position P''' corresponds to a motion position of the operating rod 3 where the operating rod 3 is predicted to arrive when the resultant strength is applied to the operating rod 3 on the current motion positions P of the operating rod 3. A specific method for calculating the predicted motion position P''' in the motion position predicting unit 1111-19' is described later.

When the speed component calculator 1111-1' has the boundary direction speed calculator 1111-17', the speed component calculator 1111-1' can further calculate the boundary direction speed as a speed component as well as the strength speed, the boundary line arrival speed, and the central direction speed.

II. Configuration of Motion Speed Calculator

Figure 14B:
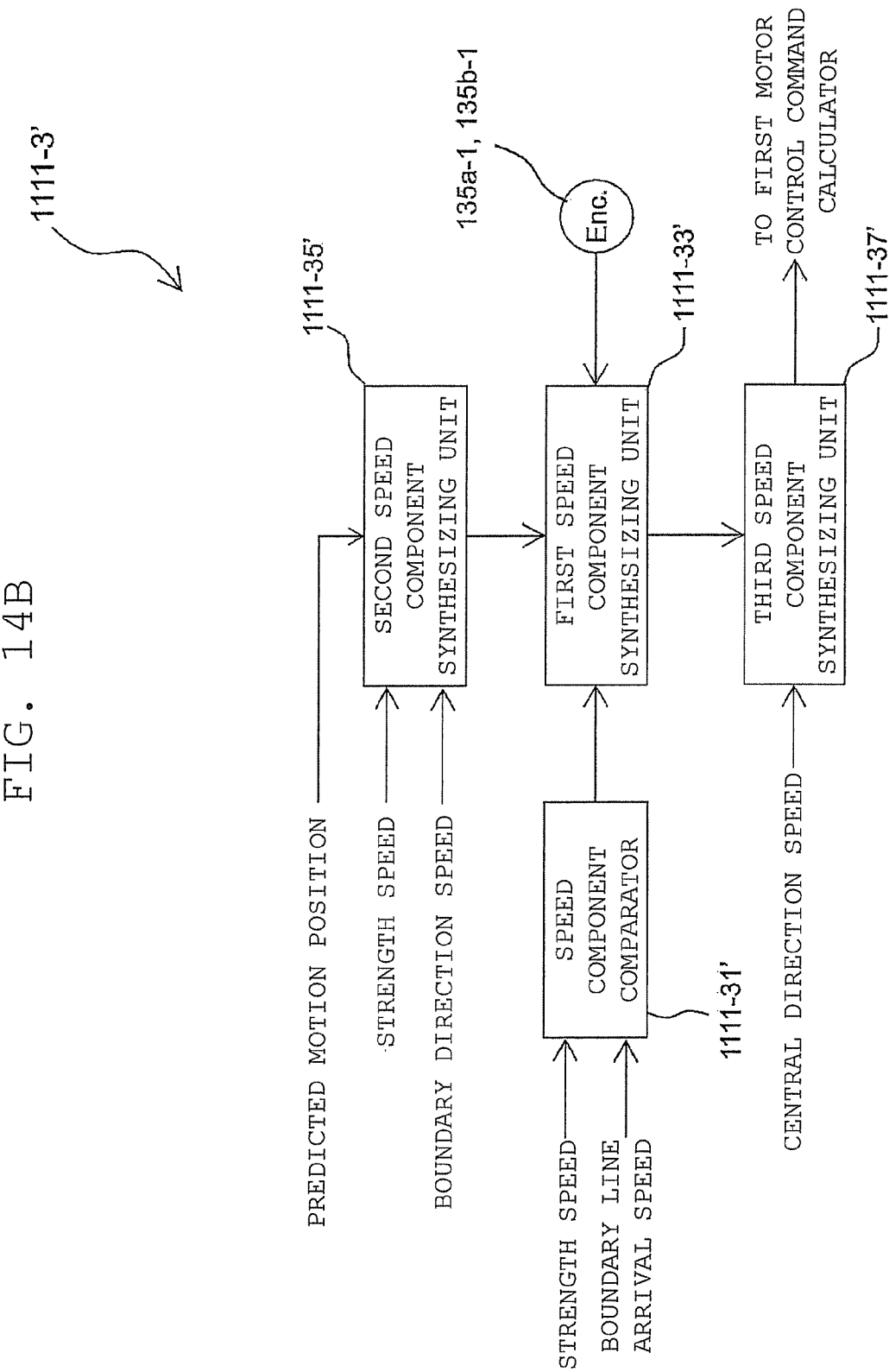
FIG. 14B is a diagram illustrating a configuration of a motion speed calculator of the training apparatus according to the second embodiment.

The configuration of the motion speed calculator 1111-3' of the training apparatus 200 according to the second embodiment is described below with reference to FIG. 14B. FIG. 14B is a diagram illustrating the configuration of the motion speed calculator of the training apparatus according to the second embodiment. The motion speed calculator 1111-3' of the training apparatus 200 according to the second embodiment includes a speed component comparator 1111-31', a first speed component synthesizing unit 1111-33', a second speed component synthesizing unit 1111-35', and a third speed component synthesizing unit 1111-37'. Since the configuration and the function of the speed component comparator 1111-31' are the same as those of the speed component comparator 1111-31 in the first embodiment, description thereof is omitted.

The first speed component synthesizing unit 1111-33' synthesizes any lower one of the strength speed and the boundary line arrival speed, selected by the speed component comparator 1111-31', with a speed input from the second speed component synthesizing unit 1111-35' (described later) so as to calculate a first synthesis speed. Specifically, the first speed component synthesizing unit 1111-33' synthesizes the lower one of the strength speed and the boundary line arrival speed with the speed input from the second speed component synthesizing unit 1111-35' in a first ratio that changes based on the current motion position P of the operating rod 3. A specific method for calculating the first synthesis speed in the first speed component synthesizing unit 1111-33' is described in detail later.

The second speed component synthesizing unit 1111-35' synthesizes the strength speed with the boundary direction speed input from the speed component calculator 1111-1' in a second ratio that changes based on the predicted motion position P''' so as to calculate a speed to be output. A method for calculating the speed in the second speed component synthesizing unit 1111-35' is described later.

The third speed component synthesizing unit 1111-37' calculates a final motion speed, and outputs it to a first motor control command calculator 1111-5. A method for calculating the motion speed in the third speed component synthesizing unit 1111-37' is described in detail later.

(2) Operation of Training Apparatus According to Second Embodiment

I. Method for Calculating Boundary Direction Speed

Figure 15A:
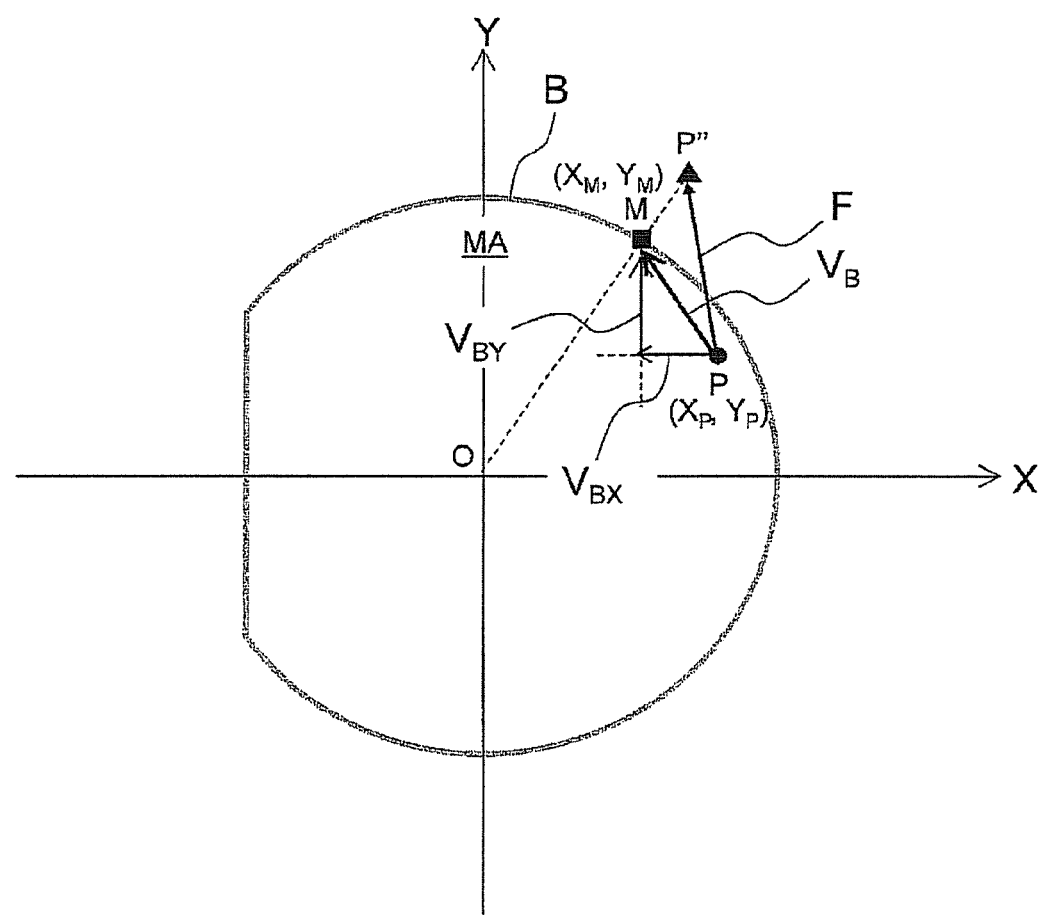
FIG. 15A is a diagram schematically illustrating a method for calculating a boundary direction speed.
Figure 15B:
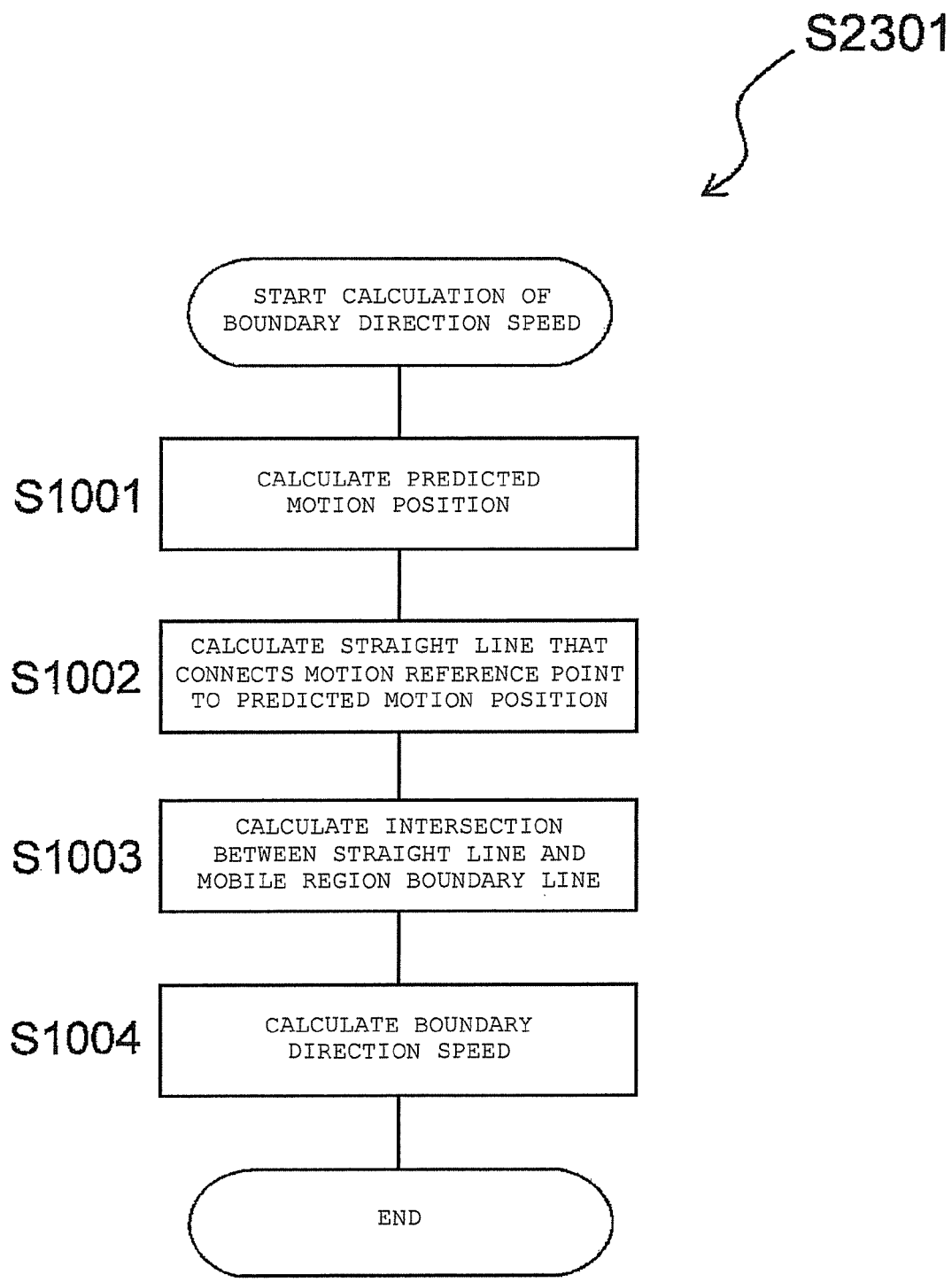
FIG. 15B is a flowchart illustrating a method for calculating the boundary direction speed.

The operation of the training apparatus 200 according to the second embodiment is described below. The method for calculating the boundary direction speed in the boundary direction speed calculator 1111-17' is described with reference to FIG. 15A and FIG. 15B. FIG. 15A is a diagram schematically illustrating the method for calculating the boundary direction speed. FIG. 15B is a flowchart illustrating the method for calculating the boundary direction speed. The boundary direction speed is calculated specifically in the following manner.

The motion position predicting unit 1111-19' calculates the resultant strength (a resultant strength signal), and calculates the predicted motion position P''' using the calculated resultant strength (step S1001). Specifically, as illustrated in FIG. 15A, a terminal position of a resultant strength vector F (in FIG. 15A, an end denoted by an arrow) when the resultant strength vector F is extended from the current motion position P of the operating rod 3 is calculated as the predicted motion position P'''.

The magnitude of the resultant strength vector F becomes a distance along which the operating rod 3 moves when the motion speed of the operating rod 3 (the strength speed) is assumed to continue for a constant time. The motion speed of the operating rod 3 is a speed when the strength corresponding to the input resultant strength signal is applied to the operating rod 3. In this case, when the resultant strength is applied to the operating rod 3, the predicted motion position P''' is calculated as a position where the operating rod 3 is predicted to arrive. Such a resultant strength vector F can be calculated as, for example, a product of the resultant strength signal and a predetermined coefficient. As a result, the position at the time when the operating rod 3 moves at the strength speed for the constant time can be predicted as the predicted motion position P'''.

In another manner, the resultant strength vector F may be calculated as, for example, a vector that connects the current motion position P and a position where the operating rod 3 is decelerated from the strength speed at a predetermined deceleration and is expected to stop (decelerated to stop). That is, the predicted motion position P''' may be a position where the operating rod 3 is decelerated to stop from the strength speed at the predetermined deceleration. As a result, a position where the operating rod 3 finally stops can be predicted as the predicted motion position P'''.

The boundary direction speed calculator 1111-17' calculates a straight line that connects a motion position reference point O and the predicted motion position P''' (a line segment OP''' indicated by a dotted line in FIG. 15A) (step S1002). An intersection M between the straight line and the mobile region boundary line B is calculated (step S1003). A coordinate of the intersection M can be calculated by, for example, solving simultaneous equations of an equation representing the straight line (the line segment OP''') and an equation representing the mobile region boundary line B.

After the intersection M is calculated, the boundary direction speed calculator 1111-17' calculates the boundary direction speed $V_B$ based on a location deviation between the intersection M and the current motion position P of the operating rod 3 (step S1004). Specifically, an X-axis component $V_{BX}$ of the boundary direction speed $V_B$ is calculated as a speed at which the operating rod 3 moves from an X coordinate value $X_P$ of the motion position P to an X coordinate value $X_M$ of the intersection M at a constant deceleration. That is, the magnitude of $V_{BX}$ is calculated according to a formula that is proportional to a square root of an absolute value of a location deviation $X_P$ (an X coordinate value of the motion position P)—$X_M$ (the X coordinate value of the intersection M). Further, a direction of $V_{BX}$ can be determined based on a magnitude relationship between the X coordinate value $X_P$ of the motion position P and the X coordinate value $X_M$ of the intersection M.

On the other hand, a Y-axis component $V_{BY}$ of the boundary direction speed $V_B$ is calculated as a speed at which the operating rod 3 moves from a Y coordinate value $Y_P$ of the motion position P to a Y coordinate value $Y_M$ of the intersection M at a constant deceleration. Specifically, a magnitude of the Y-axis component $V_{BY}$ of the boundary direction speed $V_B$ is calculated according to a formula that is proportional to a square root of an absolute value obtained by a location deviation $Y_P$ (the Y coordinate value of motion position P)—$Y_M$ (the Y coordinate value of the intersection M). Further, a direction of $V_{BY}$ is determined based on a magnitude relationship between the Y coordinate value $Y_P$ of the motion position P and the Y coordinate value $Y_M$ of the intersection M.

As illustrated in FIG. 15A, the boundary direction speed $V_B$ obtained by synthesizing the X-axis component $V_{BX}$ and the Y-axis component $V_{BY}$ can be calculated as a speed of a direction along the mobile region boundary line B from the current motion position P of the operating rod 3 to the intersection M.

As described above, the boundary direction speed is calculated by using the intersection M. Therefore, when the predicted motion position P''' is inside an operating rod mobile region MA, the intersection M is not present. In this case, the boundary direction speed cannot be calculated. Therefore, when the predicted motion position P''' is inside the operating rod mobile region MA, the boundary direction speed calculator 1111-17' may calculate the boundary direction speed as 0, or may end the process for calculating the boundary direction speed without calculating the boundary direction speed.

II. Method for Calculating First Synthesis Speed

Figure 16A:
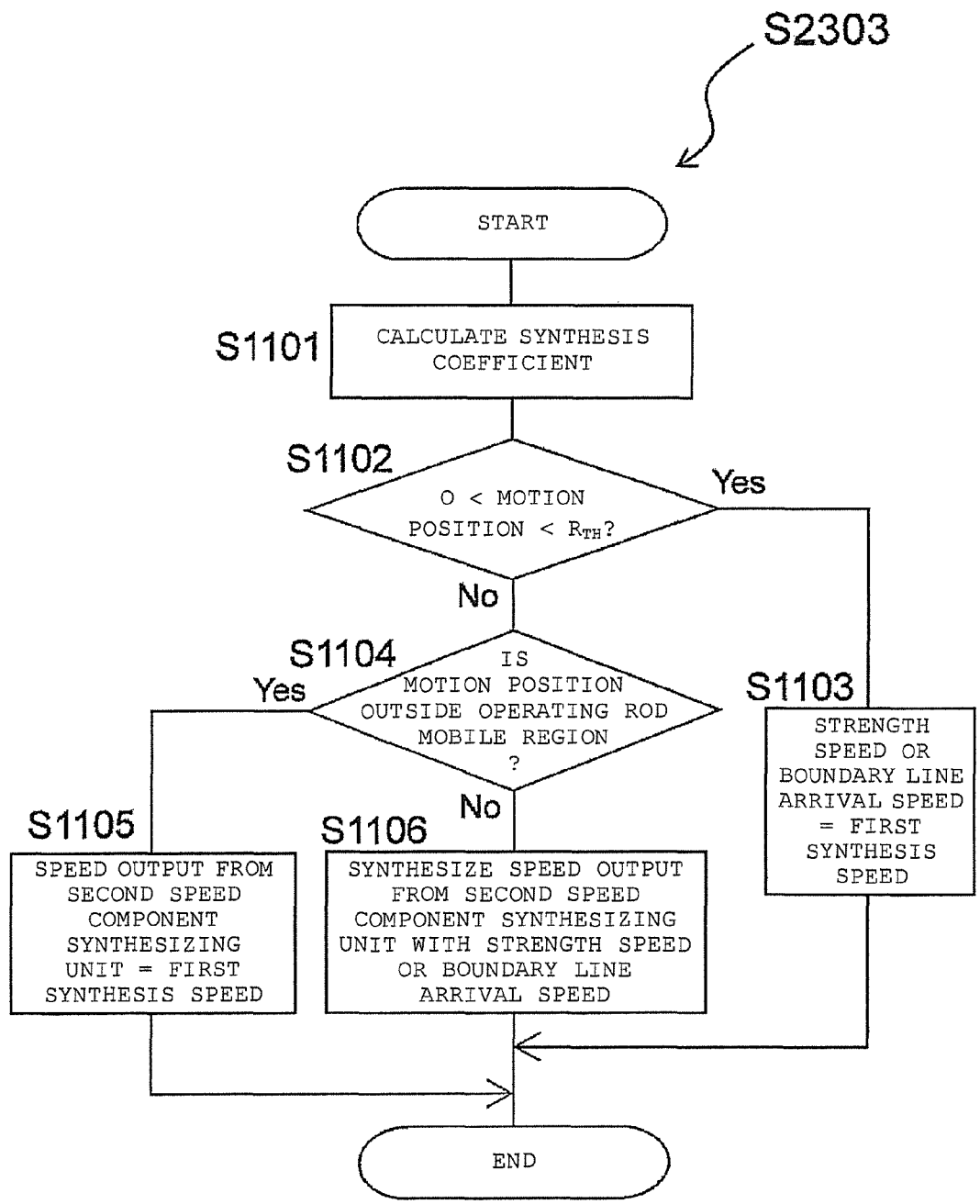
FIG. 16A is a flowchart illustrating a method for calculating a first synthesis speed in a first speed component synthesizing unit.

The method for calculating the first synthesis speed in the first speed component synthesizing unit 1111-33' is described below with reference to FIG. 16A. FIG. 16A is a flowchart illustrating the method for calculating the first synthesis speed in the first speed component synthesizing unit. In this embodiment, the first speed component synthesizing unit 1111-33' calculates a sum of a product of any lower one of the strength speed and the boundary line arrival speed and a first synthesis coefficient and a product of the speed input from the second speed component synthesizing unit 1111-35' and a second synthesis coefficient as the first synthesis speed. That is, the first synthesis speed is defined as a speed obtained by synthesizing any lower one of the strength speed and the boundary line arrival speed with the speed input from the second speed component synthesizing unit 1111-35' in a first ratio (the first synthesis coefficient/the second synthesis coefficient).

Specifically, the first speed component synthesizing unit 1111-33' calculates the first synthesis coefficient and the second synthesis coefficient based on the current motion position P of the operating rod 3 (step S1101). In this embodiment, the first synthesis coefficient and the second synthesis coefficient are calculated as illustrated in FIG. 16B. FIG. 16B is a diagram illustrating a relationship between the first synthesis coefficient and the second synthesis coefficient, and a distance from the motion position reference point O to the motion position P. As illustrated in FIG. 16B, the first synthesis coefficient (a doted line in FIG. 16B) is 1 when the current motion position P of the operating rod 3 is within a range from the motion position reference point O to a boundary-direction speed synthesis starting position $R_{TH}$. Further, when the motion position P of the operating rod 3 is within a range from the boundary-direction speed synthesis starting position $R_{TH}$ to the mobile region boundary line B, the first synthesis coefficient monotonically decreases from 1 to 0. Further, when the motion position P of the operating rod 3 is outside the operating rod mobile region MA, the first synthesis coefficient is 0.

The second synthesis coefficient (a solid line in FIG. 163) is, contrary to the first synthesis coefficient, 0 when the current motion position P of the operating rod 3 is between the motion position reference point O and the boundary-direction speed synthesis starting position $R_{TH}$. When the motion position P of the operating rod 3 is within the range from the boundary-direction speed synthesis starting position $R_{TH}$ to the mobile region boundary line B, the second synthesis coefficient monotonically increases from 0 to 1. Further, when the motion position P of the operating rod 3 is outside the operating rod mobile region MA, the second synthesis coefficient is 1.

Further, the first synthesis coefficient and the second synthesis coefficient (the first ratio) may be calculated as illustrated in FIG. 16B based on a distance between the mobile region boundary line B and the current motion position P of the operating rod 3. As a result, as to the operating rod mobile region MA of any shape other than the circular shape, the first synthesis coefficient and the second synthesis coefficient can be determined.

After the first synthesis coefficient and the second synthesis coefficient are calculated, the first speed component synthesizing unit 1111-33' determines whether the current motion position P of the operating rod 3 is within the range from the motion position reference point O to the boundary-direction speed synthesis starting position $R_{TH}$ (step S1102). When the determination is made that the current motion position P of the operating rod 3 is within the range from the motion position reference point O to the boundary-direction speed synthesis starting position $R_{TH}$ ("Yes" at step S1102), the first speed component synthesizing unit 1111-33' calculates any lower one of the boundary line arrival speed and the strength speed as the first synthesis speed (step S1103). This is because when the motion position P of the operating rod 3 is within the range from the motion position reference point O to the boundary-direction speed synthesis starting position $R_{TH}$, the first synthesis coefficient is calculated as 1, and the second synthesis coefficient is calculated as 0.

On the other hand, when the determination is made that the current motion position P of the operating rod 3 is outside the range from the motion position reference point O to the boundary-direction speed synthesis starting position $R_{TH}$ ("No" at step S1102), the first speed component synthesizing unit 1111-33' further determines whether the current motion position P is outside the operating rod mobile region MA (here, also "on the mobile region boundary line B" is included in "outside the operating rod mobile region MA) (step S1104).

When the determination is made that the motion position P of the operating rod 3 is outside the operating rod mobile region MA ("Yes" at step S1104), the first speed component synthesizing unit 1111-33' calculates the speed output from the second speed component synthesizing unit 1111-35' as the first synthesis speed (step S1105). This is because, in this case, the first synthesis coefficient is calculated as 0 and the second synthesis coefficient is calculated as 1.

On the other hand, when the determination is made that the motion position P of the operating rod 3 is on a position closer to the mobile region boundary line B than the boundary-direction speed synthesis starting position $R_{TH}$ inside the operating rod mobile region MA, namely, the motion position P of the operating rod 3 is near the mobile region boundary line B ("No" at step S1104), both the first synthesis coefficient and the second synthesis coefficient obtain values in a range from 0 to 1. Therefore, the first speed component synthesizing unit 1111-33' synthesizes any lower one of the strength speed and the boundary line arrival speed with the speed output from the second speed component synthesizing unit 1111-35' in the first ratio so as to calculate the first synthesis speed (step S1106).

Steps S1101 to S1106 are executed, so that the first speed component is calculated as follows based on the current motion position P of the operating rod 3.

(I) When the current motion position P of the operating rod 3 is within the range from the motion position reference point O to the boundary-direction speed synthesis starting position $R_{TH}$, the lower one of the strength speed and the boundary line arrival speed becomes the first synthesis speed (step S1103). That is, when the current motion position P of the operating rod 3 is sufficiently inside the operating rod mobile region MA, similarly to the first embodiment, the lower one of the strength speed and the boundary line arrival speed is calculated as the first synthesis speed.

(II) When the current motion position P of the operating rod 3 is closer to the mobile region boundary line B than the boundary-direction speed synthesis starting position $R_{TH}$ inside the operating rod mobile region MA, namely, when the current motion position P of the operating rod 3 is near the mobile region boundary line B, the lower one of the strength speed and the boundary line arrival speed is synthesized with the speed output from the second speed component synthesizing unit 1111-35' in the first ratio so that the first synthesis speed is calculated (step S1106).

(III) When the current motion position P of the operating rod 3 is outside the operating rod mobile region MA (including the mobile region boundary line B), the speed output from the second speed component synthesizing unit 1111-35' is calculated as the first synthesis speed (step S1105).

Further, as illustrated in FIG. 16B, since the first synthesis coefficient and the second synthesis coefficient continuously change, a rate of the speed output from the second speed component synthesizing unit 1111-35' and a rate of the strength speed or the boundary line arrival speed at the first synthesis speed continuously change with respect to the motion position P of the operating rod 3. As a result, the first synthesis speed is prevented from abruptly changing, and the operating rod 3 can be moved smoothly.

III. Method for Calculating Speed in Second Speed Component Synthesizing Unit

Figure 17A:
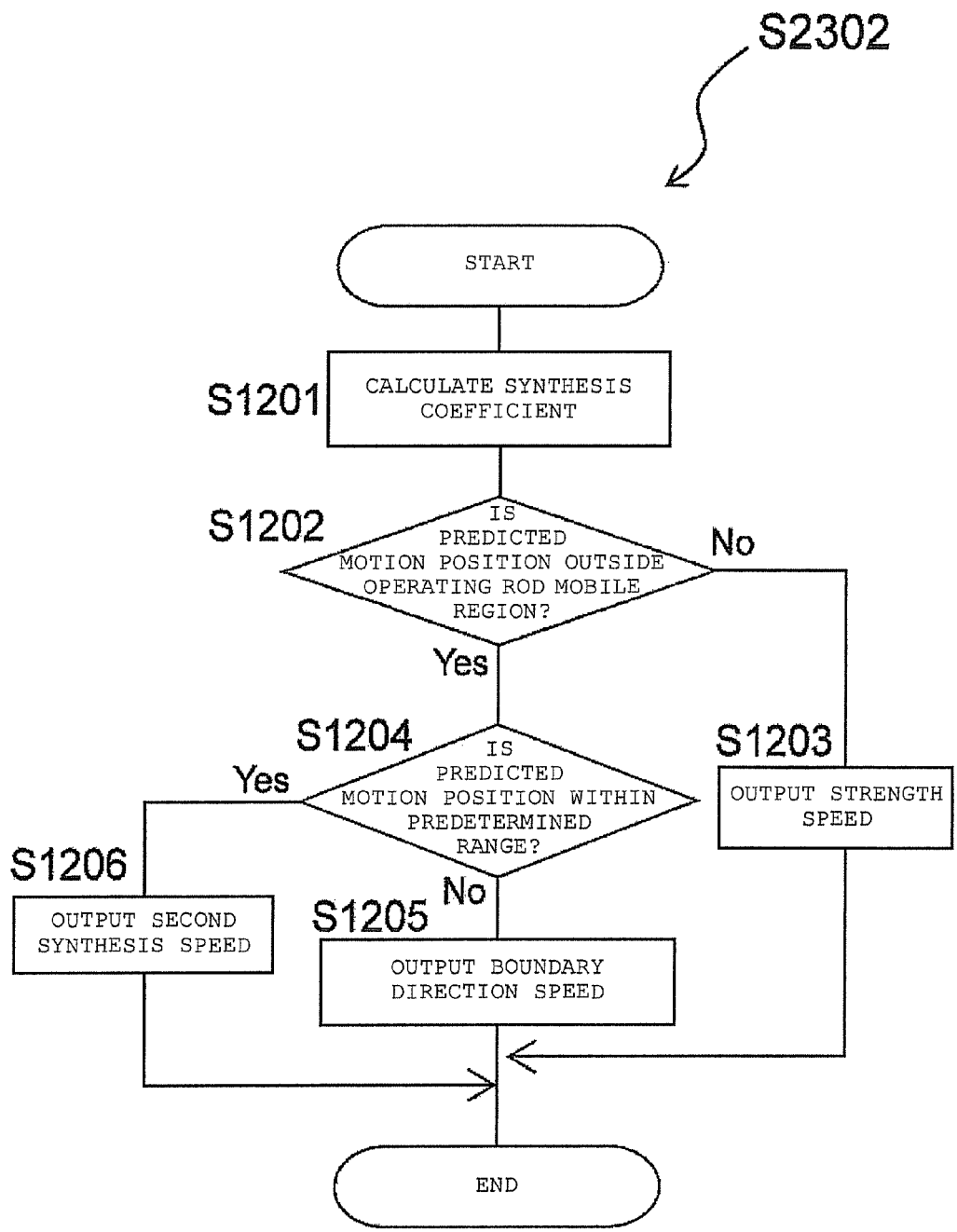
FIG. 17A is a flowchart illustrating a method for calculating a speed in a second speed component synthesizing unit.

The method for calculating the speed in the second speed component synthesizing unit 1111-35' is described below with reference to FIG. 17A. FIG. 17A is a flowchart illustrating the method for calculating the speed in the second speed component synthesizing unit. The second speed component synthesizing unit 1111-35' calculates the speed by summing a product of the strength speed and a third synthesis coefficient and a product of the boundary direction speed and a fourth synthesis coefficient.

Specifically, the second speed component synthesizing unit 1111-35' calculates the third synthesis coefficient and the fourth synthesis coefficient illustrated in FIG. 17B based on the predicted motion position P''' (step S1201). FIG. 17B is a diagram illustrating a relationship between the third synthesis coefficient and the fourth synthesis coefficient and a distance from the motion position reference point to the predicted motion position.

As illustrated in FIG. 17B, the third synthesis coefficient (a dotted line in FIG. 17B) is 1 when the predicted motion position P''' is within the operating rod mobile region MA. When the predicted motion position P''' is outside the operating rod mobile region MA, as a distance between the mobile region boundary line B and the predicted motion position P''' increases, the third synthesis coefficient monotonically decreases. When the predicted motion position P''' is on a position farther than the predetermined position outside the operating rod mobile region MA, the third synthesis coefficient becomes 0.

On the other hand, the fourth synthesis coefficient (a solid line in FIG. 17B) is 0 when the predicted motion position P''' is within the operating rod mobile region MA. When the predicted motion position P''' is outside the operating rod mobile region MA, the fourth synthesis coefficient monotonically increases as distance from the mobile region boundary line B to the predicted motion position P''' increases. When the predicted motion position P''' is on a position farther than the predetermined position outside the operating rod mobile region MA, the fourth synthesis coefficient is 1.

Further, the third synthesis coefficient and the fourth synthesis coefficient (the second ratio) may be calculated as illustrated in FIG. 17B based on the distance between the mobile region boundary line B and the predicted motion position P'''. As a result, in the operating rod mobile region MA of any shape other than the circular shape, the third synthesis coefficient and the fourth synthesis coefficient can be determined.

After the third synthesis coefficient and the fourth synthesis coefficient are calculated, the second speed component synthesizing unit 1111-35' determines whether the predicted motion position P''' is outside the operating rod mobile region MA (step S1202). When the determination is made that the predicted motion position P''' is inside the operating rod mobile region MA ("No" at step S1202), the third synthesis coefficient is calculated as 1, and the fourth synthesis coefficient is calculated as 0. Therefore, the second speed component synthesizing unit 1111-35' outputs the strength speed (step S1203).

On the other hand, when the determination is made that the predicted motion position P''' is outside the operating rod mobile region MA ("Yes" at step S1202), the second speed component synthesizing unit 1111-35' further determines whether the predicted motion position P''' is within a range from the mobile region boundary line B to the predetermined position (the predetermined range in FIG. 17B) (step S1204).

When the predicted motion position P''' is on an outer side with respect to the predetermined range illustrated in FIG. 17B ("No" at step S1204), the third synthesis coefficient is calculated as 0, and the fourth synthesis coefficient is calculated as 1. Therefore, in this case, the second speed component synthesizing unit 1111-35' outputs the boundary direction speed (step S1205).

On the other hand, when the predicted motion position P''' is within the predetermined range illustrated in FIG. 17B ("Yes" at step S1204), both the third synthesis coefficient and the fourth synthesis coefficient obtain values ranging from 0 to 1. Therefore, the second speed component synthesizing unit 1111-35' outputs a second synthesis speed obtained by synthesizing the strength speed with the boundary direction speed in the second ratio (step S1206).

Steps S1201 to S1206 are executed so that the second speed component synthesizing unit 1111-35' outputs the following speed according to a location of the predicted motion position P'''.

(IV) When the predicted motion position P''' is within the operating rod mobile region MA, namely, when the operating rod 3 is predicted not to move outside the operating rod mobile region MA due to a current strength, the second speed component synthesizing unit 1111-35' outputs the strength speed.

(V) When the predicted motion position P''' is within a range of the predetermined distance from the mobile region boundary line B outside the operating rod mobile region MA, namely, when the operating rod 3 is expected to move near the mobile region boundary line B outside the operating rod mobile region MA due to the current strength, the second speed component synthesizing unit 1111-35' outputs the second synthesis speed.

(VI) When the predicted motion position P''' is on a position away from the mobile region boundary line B by the predetermined distance or more, namely, when the operating rod 3 is expected to move to a position away from the operating rod mobile region MA to some extent due to the current strength, the second speed component synthesizing unit 1111-35' outputs the boundary direction speed.

Further, as illustrated in FIG. 17B, the third synthesis coefficient and the fourth synthesis coefficient continuously change with respect to the predicted motion position. As a result, the speed output from the second speed component synthesizing unit 1111-35' can be changed smoothly from the strength speed into the boundary direction speed or vice versa based on the magnitude of the predicted motion position P'''. As a result, the motion speed of the operating rod 3 is prevented from abruptly changing.

Figure 18:
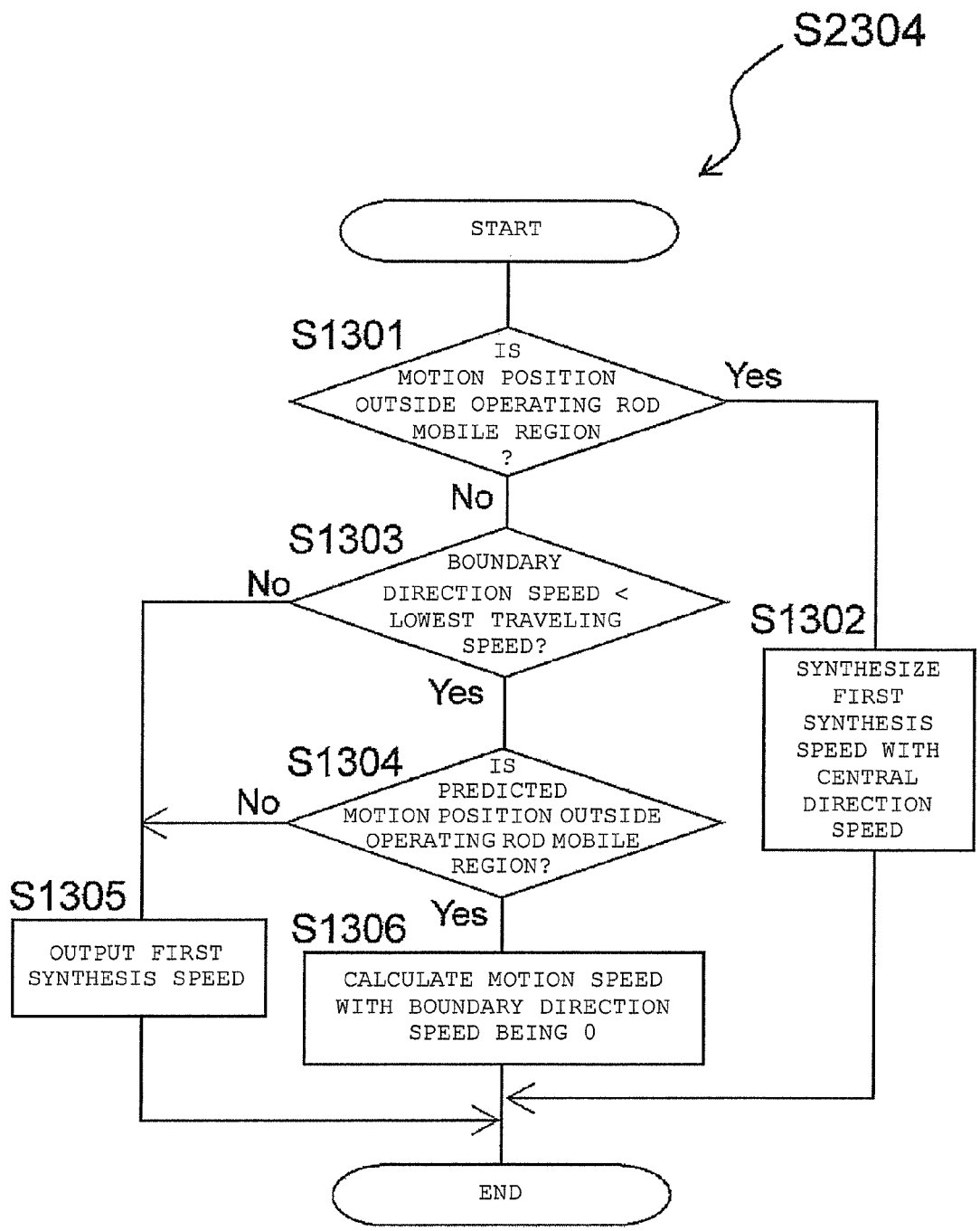
FIG. 18 is a flowchart illustrating a method for calculating a speed in a third speed component synthesizing unit.

IV. Method for Calculating Motion Speed in Third Speed Component Synthesizing Unit The method for calculating the motion speed in the third speed component synthesizing unit 1111-37' is described below with reference to FIG. 18. FIG. 18 is a flowchart illustrating the method for calculating a speed in the third speed component synthesizing unit. The third speed component synthesizing unit 1111-37' further synthesizes a speed with the first synthesis speed from the first speed component synthesizing unit 1111-33' based on existence locations of the motion position P and the predicted motion position P''' of the operating rod 3 so as to calculate a final motion speed.

Specifically, the third speed component synthesizing unit 1111-37' determines whether the motion position P of the operating rod 3 is outside the operating rod mobile region MA (step S1301). At step S1301, the mobile region boundary line B is included in the operating rod mobile region MA. When the determination is made that the motion position P of the operating rod 3 is outside the operating rod mobile region MA ("Yes" at step S1301), the third speed component synthesizing unit 1111-37' determines that the speed obtained by synthesizing the first synthesis speed with the central direction speed as the motion speed (step S1302).

On the other hand, when the determination is made that the motion position P of the operating rod 3 is inside the operating rod mobile region MA ("No" at step S1301), the third speed component synthesizing unit 1111-37' determines whether the calculated boundary direction speed is lower than a lowest traveling speed (step S1303).

When the boundary direction speed is calculated as a value that is the lowest traveling speed or more ("No" at step S1303), the third speed component synthesizing unit 1111-37' outputs the first synthesis speed as the motion speed (step S1305).

On the other hand, when the boundary direction speed is calculated to be lower than the lowest traveling speed ("Yes" at step S1303), the third speed component synthesizing unit 1111-37' further determines whether the predicted motion position P''' is outside the operating rod mobile region MA (step S1304). When the determination is made that the predicted motion position P''' is inside the operating rod mobile region MA ("No" at step S1304), the third speed component synthesizing unit 1111-37' outputs the first synthesis speed as the motion speed (step S1305). On the other hand, when the determination is made that the predicted motion position P''' is outside the operating rod mobile region MA ("Yes" at step S1304), the third speed component synthesizing unit 1111-37' calculates the motion speed with the boundary direction speed being 0 (step S1306).

Figure 19:
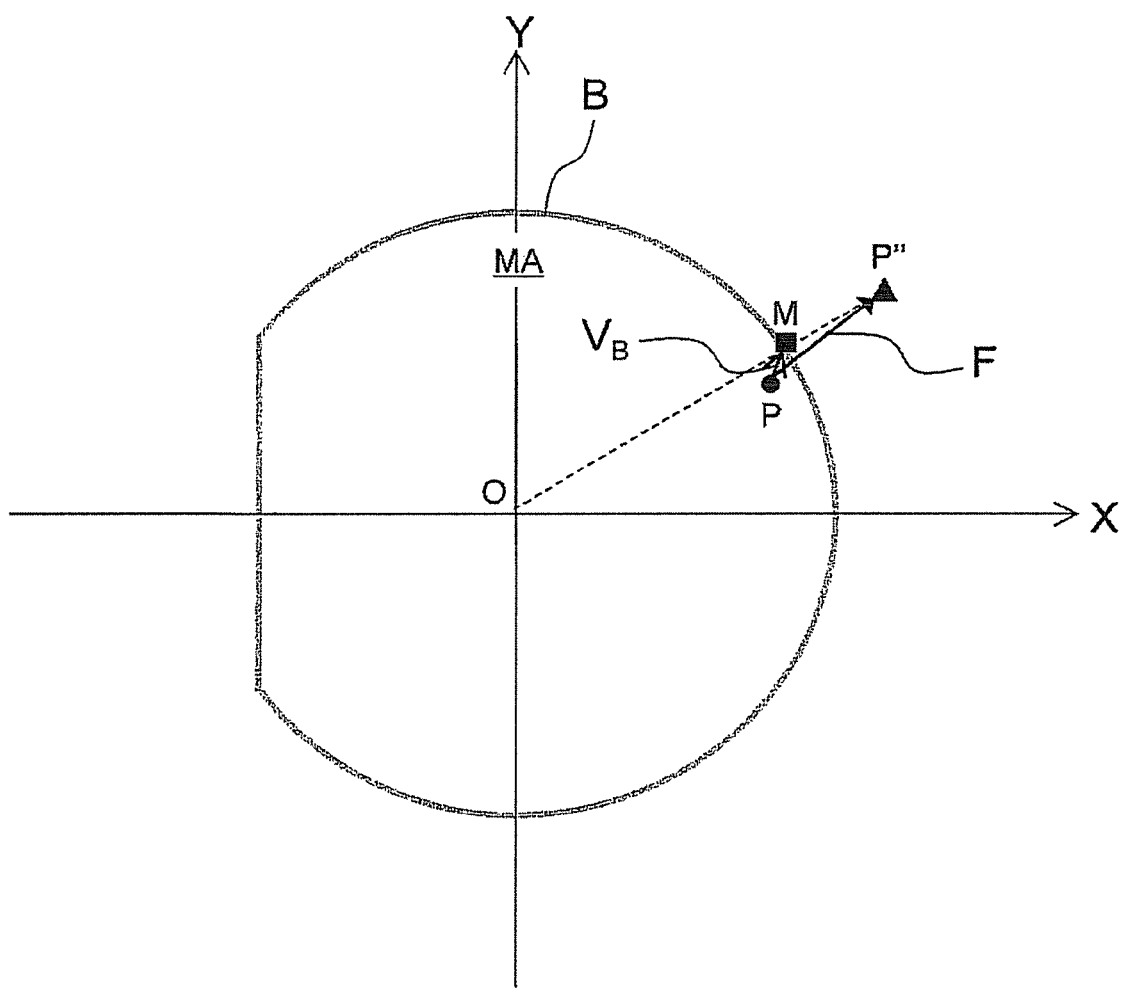
FIG. 19 is a diagram schematically illustrating one example when the boundary direction speed is calculated as a small value.

The meaning of the boundary direction speed being lower than the lowest traveling speed is now described. When the boundary direction speed is calculated as a small value, as illustrated in FIG. 19, the distance between the current motion position P of the operating rod 3 and the intersection M is short. In another case, the distance between the motion position P of the operating rod 3 and the intersection N is long, but the motion position P is present on the line segment OP'''. FIG. 19 is a diagram schematically illustrating one example of a case where the boundary direction speed is calculated as a small value.

V. Operation of Training Apparatus According to Second Embodiment

Figure 20:
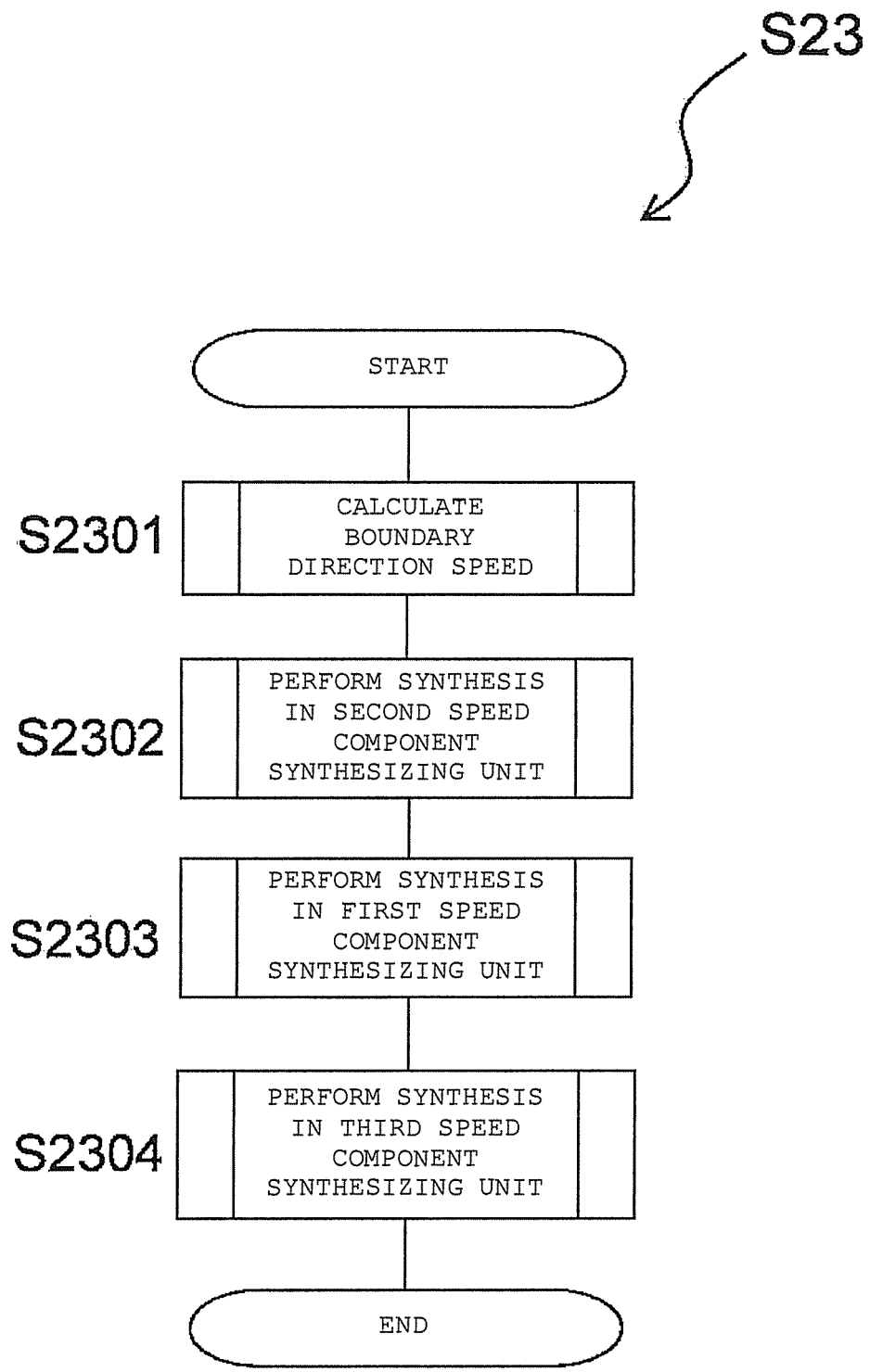
FIG. 20 is a flowchart illustrating a method for calculating the motion speed in the training apparatus according to the second embodiment.

The operation of the training apparatus 200 according to the second embodiment is described below with reference to FIG. 20. FIG. 20 is a flowchart illustrating the method for calculating the motion speed of the training apparatus according to the second embodiment. The operation of the training apparatus 200 according to the second embodiment is the same as the operation of the training apparatus 100 according to the first embodiment except for the method for calculating the motion speed during the execution of the first motion mode (corresponding to step S23 in the flowchart of FIG. 12B). Therefore, only the method for calculating the motion speed during the execution of the first motion mode in the training apparatus 200 according to the second embodiment is described below, and the description of the other parts of the operation is omitted.

When the calculation of the motion speed in the training apparatus 200 is started, the boundary direction speed calculator 1111-17' executes steps S1001 to S1004 so as to calculate the boundary direction speed in addition to the strength speed, the boundary line arrival speed, and the central direction speed calculated at step S22 (step S2301).

After the boundary direction speed is calculated, the second speed component synthesizing unit 1111-35' executes steps S1201 to S1206, and outputs the predetermined speed based on the location of the predicted motion position P''' (step S2302).

After the second speed component synthesizing unit 1111-35' outputs the predetermined speed, the first speed component synthesizing unit 1111-33' executes steps S1101 to 1106 so as to calculate the first synthesis speed (step S2303).

After the first synthesis speed is calculated, the third speed component synthesizing unit 1111-37' executes steps S1301 to S1306 so as to calculate a final motion speed based on the current motion position P and the location of the predicted motion position P''' of the operating rod 3 (step S2304).

When the above-described steps S2301 to S2304 are executed, the motion speed is calculated as follows based on the predicted motion position P''' and the current motion position P of the operating rod 3.

(I) When Current Motion Position of Operating Rod is Present inside Operating Rod Mobile Region When the current motion position P of the operating rod 3 is present inside the operating rod mobile region MA, the motion speed is calculated as follows according to the location of the predicted motion position P''' and the direction of the force applied to the operating rod 3.

(i) When the direction of the force applied to the operating rod is nearly vertical to the mobile region boundary line and the operating rod 3 moves to a position away from the operating rod mobile region MA to an extent based on the applied strength At this time, the boundary direction speed is 0. Therefore, when a force that is nearly vertical to the mobile region boundary line B is applied to the operating rod 3 on the mobile region boundary line B, the operating rod 3 can be stably stopped on the mobile region boundary line B.

(ii) When the motion position of the operating rod is sufficiently inside the operating rod mobile region When the motion position P of the operating rod 3 is closer to the motion position reference point O than the boundary-direction speed synthesis starting position $R_{TH}$, namely, when the motion position P of the operating rod 3 is sufficiently inside the operating rod mobile region MA, the motion speed of the operating rod 3 is any lower one of the strength speed and the boundary line arrival speed similarly to the training apparatus 100 according to the first embodiment.

Not limited only to the case (ii), when any lower one of the strength speed and the boundary line arrival speed is output as the motion speed, an upper limit value of the motion speed may be limited to a maximum motion speed $V_{max}$ similarly to the first embodiment. As a result, the operating rod 3 can be prevented from operating at an excessively high speed.

(iii) When the motion position of the operating rod is near the mobile region boundary line and the predicted motion position is present inside the operating rod mobile region When the motion position P of the operating rod 3 is near the mobile region boundary line B and the predicted motion position P''' is present inside the operating rod mobile region MA (namely, the operating rod 3 is not moved outside the operating rod mobile region MA by the force applied to the operating rod 3), the motion speed is the lower one of the strength speed and the boundary line arrival speed similarly to the training apparatus 100 according to the first embodiment.

That is, even if the motion position P of the operating rod 3 is near the mobile region boundary line B, when the operating rod 3 is not moved outside the operating rod mobile region MA by the force to be applied to the operating rod 3, the motion speed of the operating rod 3 is the lower one of the strength speed and the boundary line arrival speed similarly to the first embodiment.

(iv) When the motion position of the operating rod is near the mobile region boundary line and the predicted motion position is present near the mobile region boundary line outside the operating rod mobile region When the motion position P of the operating rod 3 is near the mobile region boundary line B and the predicted motion position P''' is present near the mobile region boundary line B outside the operating rod mobile region MA, the motion speed is calculated as a speed including the strength speed and the boundary direction speed or including the strength speed, the boundary direction speed, and the boundary line arrival speed.

A rate of the boundary direction speed in the motion speed is lower than a rate of the boundary direction speed in the motion speed calculated when the predicted motion position P''' is farther than the vicinity of the mobile region boundary line B, described later. This is because when the predicted motion position P''' is present near the mobile region boundary line B outside the operating rod mobile region MA, the second speed component synthesizing unit 1111-35' outputs the second synthesis speed including both the boundary direction speed and the strength speed. On the other hand, as described later, when the predicted motion position P''' is present on a position away from the mobile region boundary line B, the second speed component synthesizing unit 1111-35' outputs the boundary direction speed.

In other words, when a force that does not move the operating rod 3 far off the operating rod mobile region MA is applied to the operating rod 3 near the mobile region boundary line B, the motion speed includes the boundary direction speed, whereas the motion speed includes also the strength speed and/or the boundary line arrival speed at a comparatively high rate.

Therefore, when the motion position P of the operating rod 3 is near the mobile region boundary line B and the force applied to the operating rod 3 does not cause the operating rod 3 to be far off the operating rod mobile region MA (for example, when the magnitude of the force to be applied is weak and/or an angle (an acute angle) between a direction of the force to be applied and a tangent of the mobile region boundary line B is small), the operating rod 3 can be moved along the mobile region boundary line B and simultaneously to the direction where the force is applied.

Further, the first synthesis coefficient and the second synthesis coefficient continuously change with respect to the motion position P of the operating rod 3 (FIG. 16B), and the third synthesis coefficient and the fourth synthesis coefficient continuously change with respect to the predicted motion position P''' (FIG. 17B). As a result, the rate of the boundary direction speed in the motion speed is gradually larger as the motion position P of the operating rod 3 is farther from the motion position reference point O and/or the predicted motion position P''' is farther from the mobile region boundary line B. As a result, the motion speed can be smoothly changed from the strength speed and/or the boundary line arrival speed to the boundary direction speed or vice versa. As a result, the change in the motion speed can suppress an impact exerting on the operating rod 3.

(v) When the motion position of the operating rod is near the mobile region boundary line and the predicted motion position is on a position away from the mobile region boundary line outside the operating rod mobile region When the motion position P of the operating rod 3 is near the mobile region boundary line B and the predicted motion position P''' is present on the position away from the mobile region boundary line B outside the operating rod mobile region MA (namely, outside the predetermined range), the motion speed is calculated as a speed including the boundary direction speed and the strength speed or the boundary line arrival speed. The rate of the boundary direction speed in the motion speed calculated under this condition is larger than the rate of the boundary direction speed in the motion speed calculated under the condition (iv). That is, the influence of the boundary direction speed in the motion speed is more emphatic than that in the condition (iv).

In other words, when the current motion position P of the operating rod 3 is near the mobile region boundary line B and the force applied to the operating rod 3 makes the predicted motion position P''' deviate from the operating rod mobile region MA to an extent, the influence of the boundary direction speed is increased in the motion speed. As a result, for example, even when the force to be applied to the operating rod 3 is not extremely weak and the angle (the acute angle) between the direction of the force to be applied and the tangent of the mobile region boundary line B is large, the operating rod 3 can be restrained from moving outside the operating rod mobile region MA.

(II) When Current Motion Position of Operating Rod is on Mobile Region Boundary Line When the current motion position P of the operating rod 3 is on the mobile region boundary line B and the predicted motion position P''' is present within the predetermined range, the second synthesis speed is output as the motion speed. On the other hand, when the predicted motion position P''' is outside the predetermined range, the boundary direction speed is output as the motion speed.

In other words, when the current motion position P of the operating rod 3 is on the mobile region boundary line B, for example, when the force to be applied to the operating rod 3 is weak and the angle (the acute angle) between the direction of the force to be applied and the tangent of the mobile region boundary line B is small, the operating rod 3 is moved also in view of the force applied to the operating rod 3.

On the other hand, for example, when the force to be applied to the operating rod 3 is not extremely weak and the angle (the acute angle) between the direction of the force to be applied and the tangent of the mobile region boundary line B is large, the operating rod 3 is moved along the mobile region boundary line B.

(III) When Current Motion Position of Operating Rod is Present Outside Operating Rod Mobile Region When the current motion position P of the operating rod 3 is outside the operating rod mobile region MA, the motion speed includes the central direction speed that is a speed component toward the motion position reference point O. As a result, when the motion position P of the operating rod 3 is outside the operating rod mobile region MA, the operating rod 3 is moved inside the operating rod mobile region MA.

In the method for calculating the motion speed described in the second embodiment, the order of the operation illustrated in the flowchart may be changed or the operation may be changed without exceeding the scope of the present invention.

3. Effects of Embodiments

Effects of the first embodiment and the second embodiment are as follows.

The training apparatus according to the first embodiment (for example, the training apparatus 100) is the training apparatus for training user's four limbs including upper limbs and/or lower limbs according to the predetermined training program. The training apparatus includes the operating rod (for example, the operating rod 3), the strength detectors (for example, the Y-axis strength detector 175, the X-axis strength detector 177, and the lengthwise strength detector 393), the motion position detectors (for example, the first motion position detector 135a-1, the second motion position detector 135b-1, and the third motion position detector 359-1), the strength speed calculator (for example, the strength speed calculator 1111-11), the boundary line arrival speed calculator (for example, the boundary line arrival speed calculator 1111-13), and the motion speed calculator (for example, the motion speed calculator 1111-3).

The operating rod is supported to the stationary frame (for example, the stationary frame 1) placed on a floor surface or near the floor surface so as to be movable at 1 or more degrees of freedom. Further, the operating rod moves a held limb. The strength detector detects a strength component and outputs a strength component signal based on the detected strength component. The strength component is a component in each freedom degree direction of a strength applied to the operating rod at which the operating rod is movable. The motion position detector detects the motion positions of the operating rod (for example, the motion position P of the operating rod). The motion position of the operating rod is a position of the operating rod in each related freedom degree direction at which the operating rod is movable.

The strength speed calculator calculates a strength speed of the operating rod based on the strength component signal output from the strength detector. The boundary line arrival speed calculator calculates the boundary line arrival speed whose absolute value is smaller as a boundary line distance (for example, the boundary line distance D) is shorter. The boundary line distance is a distance from the current motion position of the operating rod to the mobile region boundary line (for example, the mobile region boundary line B). The mobile region boundary line is a boundary line for determining a boundary of the operating rod mobile region (for example, the operating rod mobile region MA). The operating rod mobile region is a region for setting a movable range of the operating rod.

The motion speed calculator calculates the lower one of the strength speed and the boundary line arrival speed as the motion speed. The motion speed is a speed at which the operating rod should operate.

In the training apparatus, the motion position detectors detect the current motion positions of the operating rod and the strength detectors detect strengths (for example, step S21). After the current motion position and strength are detected, the strength speed calculator calculates the strength speed based on the strength component signals, and the boundary line arrival speed calculator calculates the boundary line arrival speed based on the boundary line distance (for example, step S22). Thereafter, the motion speed calculator calculates the lower one of the strength speed and the boundary line arrival speed as the motion speed (for example, steps S231 to S236).

In the training apparatus, the boundary line arrival speed whose absolute value is smaller as the boundary line distance is shorter, and the strength speed based on the strength are calculated, and the lower one of the boundary line arrival speed and the strength speed is selected as the motion speed of the operating rod. That is, the motion speed of the operating rod is limited to the lowest one of the calculated speed components. Further, the motion speed is limited by the boundary line arrival speed whose absolute value is smaller as the boundary line distance is shorter particularly near the mobile region boundary line. As a result, when the operating rod arrives at the mobile region boundary line, the operating rod can be restrained from abruptly stopping to exert an impact on the limb and the operating rod can restrained from moving outside the operating rod mobile region.

Further, by selecting the lower one of the strength speed and the boundary line arrival speed as the motion speed, the motion speed can be smoothly switched from the strength speed into the boundary line arrival speed (or vice versa). As a result, the motion speed of the operating rod can be switched without exerting an impact on the limb.

The motion speed is limited to a maximum motion speed (for example, the maximum motion speed $V_{max}$) or less. The maximum motion speed is a speed for determining an upper limit value of the motion speed of the operating rod. As a result, the operating rod can be restrained from being moved at an excessively high speed.

When the determination is made that the current motion position of the operating rod is present outside the operating rod mobile region, the motion speed calculator calculates a motion speed including the speed component (for example, the central direction speed) directed toward the motion position reference point (for example, the motion position reference point O) (for example, step S235 and step S236). The motion position reference point is a reference point of the motion position of the operating rod. As a result, the operating rod can be restrained from being further moved outside the operating rod mobile region, and the operating rod can be restrained from being disabled while the current motion position of the operating rod is present outside the operating rod mobile region. Further, the operating rod outside the operating rod mobile region is returned into the operating rod mobile region.

The training apparatus according to the second embodiment (for example, the training apparatus 200) includes the operating rod (for example, the operating rod 3), the strength detectors (for example, the Y-axis strength detector 175, the X-axis strength detector 177, and the lengthwise strength detector 393), the motion position detectors (for example, the first motion position detector 135a-1, the second motion position detector 135b-1, and the third motion position detector 359-1), the boundary direction speed calculator (for example, the boundary direction speed calculator 1111-17'), the motion position predicting unit (for example, the motion position predicting unit 1111-19'), and the motion speed calculator (for example, the motion speed calculator 1111-3').

The operating rod is supported to the stationary frame placed on a floor surface or near the floor surface so as to be movable at 2 or more degrees of freedom. Further, the operating rod moves a held limb. Each of the plurality of strength detectors detects the strength component and calculates the detected strength component as a strength component signal. The strength component is a component in each freedom degree direction of a strength applied to the operating rod at which the operating rod is movable. The motion position detector detects a motion position of the operating rod. The motion position of the operating rod is a motion position in each related freedom degree direction at which the operating rod is movable.

The boundary direction speed calculator calculates a boundary direction speed. The boundary direction speed is a speed component along the mobile region boundary line (for example, the mobile region boundary line B). The mobile region boundary line is a boundary line for determining a boundary of the operating rod mobile region (for example, the operating rod mobile region MA). The operating rod mobile region is a region for setting a movable range of the operating rod. The motion position predicting unit predicts the predicted motion position (for example, the predicted motion position P'''). The predicted motion position is the motion position of the operating rod where the operating rod is predicted to arrive when a resultant strength is applied to the operating rod on a current motion position of the operating rod. The resultant strength is a strength to be obtained by synthesizing the strength components in the respective freedom degree directions. When the predicted motion position is predicted to be outside the operating rod mobile region, the motion speed calculator calculates a speed including the boundary direction speed as the motion speed. The motion speed is a speed at which the operating rod should operate.

In the training apparatus according to the second embodiment, the current motion position of the operating rod and the strength component of the strength to be applied to the operating rod are detected (for example, step S21). The motion position predicting unit predicts the predicted motion position where the operating rod arrives when the resultant strength is applied to the operating rod on the current motion position of the operating rod. When the predicted motion position is predicted to be present outside the operating rod mobile region, the motion speed calculator calculates the speed including the boundary direction speed calculated by the boundary direction speed calculator as the motion speed (for example, steps S2301 to S2304).

In the training apparatus according to the second embodiment, when the operating rod is predicted to be present outside the operating rod mobile region as a result of applying the resultant strength to the operating rod, the speed including the boundary direction speed that is a speed component along the mobile region boundary line is calculated as the motion speed. That is, when the operating rod is moved outside the operating rod mobile region by the force applied to the operating rod, the operating rod is moved along the mobile region boundary line. As a result, a natural motion along the mobile region boundary line with respect to the applied force can be realized near the boundary of the operating rod mobile region.

The boundary direction speed calculator calculates the boundary direction speed based on the location deviation between the intersection between the straight line for connecting the motion position reference point (for example, the motion position reference point O) to the predicted motion position, and the mobile region boundary line (for example, the intersection M) and the current motion position of the operating rod (for example, steps S1001 to S1004). The motion position reference point is a reference point of the motion position of the operating rod. As a result, the boundary direction speed can be calculated as a speed in a direction along the mobile region boundary line from the current motion position of the operating rod to the intersection.

The training apparatus according to the second embodiment further includes the strength speed calculator (for example, the strength speed calculator 1111-11') and the boundary line arrival speed calculator (for example, the boundary line arrival speed calculator 1111-13'). The strength speed calculator calculates the strength speed of the operating rod based on the strength component signals output from the plurality of strength detectors. The boundary line arrival speed calculator calculates the boundary line arrival speed based on the boundary line distance from the current motion position of the operating rod to the mobile region boundary line (for example, the boundary line distance D). In this case, the motion speed calculator synthesizes the boundary direction speed with the boundary line arrival speed and/or the strength speed so as to calculate the motion speed (for example, steps S2301 to S2304). As a result, the motion speed including the boundary direction speed and the boundary line arrival speed and/or the strength speed can be calculated.

The predicted motion position may be a position where the operating rod is predicted to arrive if the strength speed is kept for a fixed time. As a result, a position where the operating rod moves at the strength speed for a fixed time can be predicted as the predicted motion position.

The predicted motion position may be a position where the operating rod is predicted to decelerate to stop at a predetermined deceleration speed from the strength speed. As a result, a position where the operating rod finally stops can be predicted as the predicted motion position.

The motion speed calculator calculates the first synthesis speed as the motion speed (for example, steps S1101 to S1106). The first synthesis speed is a speed obtained by synthesizing any lower one of the strength speed and the boundary line arrival speed with the boundary direction speed or the second synthesis speed in the first ratio. The second synthesis speed is a speed including the boundary direction speed and the strength speed. The first ratio changes based on the current motion position. As a result, the motion speed obtained by synthesizing the boundary direction speed with the strength speed or the boundary line arrival speed in a suitable ratio can be calculated according to the current motion position of the operating rod. As a result, an influence of the boundary direction speed and an influence of the strength speed or the boundary line arrival speed are gradually changed so that the operating rod can be moved smoothly.

The first ratio may be calculated based on a distance between the mobile region boundary line and the current motion position of the operating rod. As a result, the first ratio can be determined for the mobile region boundary line of any shape.

The second synthesis speed is calculated by synthesizing the strength speed with the boundary direction speed in the second ratio (for example, step S1206). The second ratio changes based on the predicted motion position. As a result, depending on the force applied to the operating rod, while the operating rod is being moved preferably to the direction where the force is applied to the operating rod, natural motions of the operating rod can be realized along the mobile region boundary line with respect to the applied forces near the boundary of the operating rod mobile region.

The second ratio may be calculated based on a distance between the mobile region boundary line and the predicted motion position. As a result, the second ratio can be determined for the mobile region boundary line of any shape.

When the boundary direction speed is lower than the lowest traveling speed (for example, "Yes" at step S1303) and the predicted motion position is outside the operating rod mobile region (for example, "Yes" at step S1304), the motion speed calculator calculates a speed at which the operating rod arrives at the mobile region boundary line, and the boundary direction speed to 0 (for example, step S1306). As a result, the operating rod can be stopped stably on the mobile region boundary line. Further, when the operating rod goes slightly out of the operating rod mobile region due to a control delay, the speed toward the motion position reference point exerts until entry into the operating rod mobile region. For this reason, the operating rod quickly moves to the mobile region boundary line (for example, step S1302).

The calculating method according to the second embodiment is a method for calculating the motion speed of the operating rod at which a held limb is moved in the training apparatus for training any one of user's upper limbs and/or lower limbs according to the predetermined training program. The calculating method includes a step of detecting the current motion position of the operating rod (for example, step S21), a step of detecting the strength components of the strength applied to the operating rod in the respective freedom degree directions (for example, step S21), a step of predicting the predicted motion position at which the operating rod arrives when the resultant strength is applied to the operating rod in a current motion position (for example, step S1001), and a step of calculating the speed including the boundary direction speed as the motion speed when the predicted motion position is predicted to be outside the operating rod mobile region (for example, steps S2301 to S2304).

When the motion speed of the operating rod is calculated by the calculating method including the above steps, the operating rod can be moved along the mobile region boundary line.

The step of calculating the speed including the boundary direction speed as the motion speed includes a step of calculating the straight line for connecting the motion position reference point with the predicted motion position (for example, step S1002), a step of calculating the intersection between the straight line and the mobile region boundary line (for example, step S1003), and a step of calculating the boundary direction speed based on the location deviation between the intersection and the current motion position of the operating rod (for example, step S1004).

When the boundary direction speed is calculated by the calculating method including the above steps, the boundary direction speed can be calculated as a speed in a direction along the mobile region boundary line toward the intersection. As a result, a natural motion along the mobile region boundary line with respect to the applied force can be realized near the boundary of the operating rod mobile region.

4. Other Embodiments

The above describes embodiments of the present invention, but the present invention is not limited to the above embodiments, and various modifications can be made without departing from the subject-matter of the invention. Particularly, the plurality of embodiments and the alternative embodiments described in this specification can be arbitrarily combined.

(A) Another Embodiment of Boundary Direction Speed

In the training apparatus 200 according to the second embodiment, the boundary direction speed is calculated as a speed directed from the current motion position P of the operating rod 3 to an intersection M as illustrated in FIG. 15A. However, not limited to this, a plurality of target points may be provided between the current motion position P and the intersection M, and the boundary direction speeds at which the operating rod 3 passes through the target points may be calculated.

Figure 21:
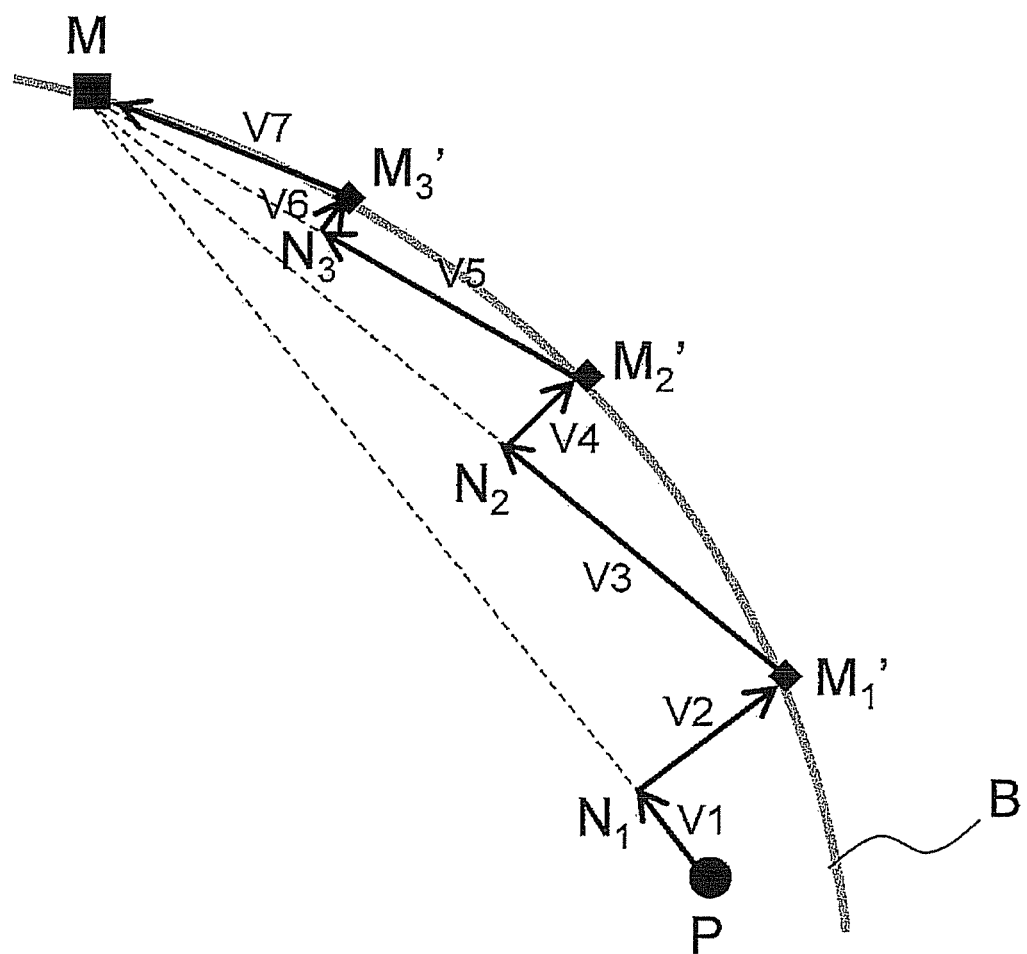
FIG. 21 is a diagram schematically illustrating the boundary direction speed according to another embodiment.

For example, as illustrated in FIG. 21, a plurality of target points $M_1'$, $M_2'$, $M_3'$, . . . may be provided on the mobile region boundary line B from the current motion position P of the operating rod 3 to the intersection M at predetermined intervals, and a plurality of speeds may be calculated as the boundary direction speed so that the operating rod 3 passes through the target points. FIG. 21 is a diagram schematically illustrating another embodiment of the boundary direction speed.

Specifically, for example, the boundary direction speed can be defined as a speed composed of a plurality of speed components such as a speed V1 of a motion to a point $N_1$ along a direction from the current motion position P to the intersection M, a speed V2 of a motion from the point $N_1$ to a target point $M_1'$ on the mobile region boundary line B, a speed V3 of a motion to a point $N_2$ along a direction from the target point $M_1'$ to the intersection M, a speed V4 of a motion from the point $N_2$ to a target point $M_2'$ on the mobile region boundary line B, and so on.

The boundary direction speed is composed of the plurality of speed components for passing through the plurality of target points on the mobile region boundary line B. As a result, as illustrated in FIG. 21, the operating rod 3 can be moved along the mobile region boundary line B so as to be closer to the mobile region boundary line B than a case where the operating rod 3 is moved from the current motion position P directly to the intersection M.

The present invention can be applied widely to training apparatuses for supporting rehabilitation of patient's upper limbs and lower limbs according to the predetermined training program.

While embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A training apparatus for training a user's four limbs including upper limbs and/or lower limbs according to a predetermined training program, the apparatus comprising:

an operating rod configured for moving a held limb, the operating rod being supported to a stationary frame placed on or near a floor surface so as to be movable at one or more degrees of freedom;

a strength detector configured for detecting a strength component that is a component of a strength applied to the operating rod in each freedom degree direction where the operating rod is movable, and outputting a strength component signal based on a magnitude of the detected strength component;

a motion position configured detector for detecting a motion position of the operating rod in the corresponding freedom degree direction where the operating rod is movable;

a strength speed calculator configured for calculating a strength speed of the operating rod based on the strength component signal output from the strength detector;

a boundary line arrival speed calculator configured for calculating a boundary line arrival speed whose absolute value is smaller as a boundary line distance is shorter, the boundary line distance being from a current motion position of the operating rod to a mobile region boundary line for defining a boundary of an operating rod mobile region for setting a range where the operating rod is movable; and a motion speed calculator configured for calculating a lower one of the strength speed and the boundary line arrival speed as a motion speed at which the operating rod is to be moved.

2. The training apparatus according to claim 1, wherein the motion speed is limited to a maximum motion speed or less.

3. The training apparatus according to claim 1, wherein when a determination is made that the current motion position of the operating rod is present outside the operating rod mobile region, the motion speed calculator calculates a motion speed including a speed component toward a motion position reference point as a reference point of the motion position of the operating rod.

4. The training apparatus according to claim 2, wherein when a determination is made that the current motion position of the operating rod is present outside the operating rod mobile region, the motion speed calculator calculates a motion speed including a speed component toward a motion position reference point as a reference point of the motion position of the operating rod.

* * * * *